US011937853B2

United States Patent
Biedermann et al.

(10) Patent No.: US 11,937,853 B2
(45) Date of Patent: Mar. 26, 2024

(54) POLYAXIAL BONE ANCHORING DEVICE AND SYSTEM INCLUDING AN INSTRUMENT AND A POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 72 days.

(21) Appl. No.: 17/466,319

(22) Filed: Sep. 3, 2021

(65) Prior Publication Data
US 2022/0054173 A1 Feb. 24, 2022

Related U.S. Application Data

(63) Continuation of application No. 16/243,794, filed on Jan. 9, 2019, now Pat. No. 11,123,108.
(Continued)

(30) Foreign Application Priority Data

Jan. 10, 2018 (EP) .................................. 18151105

(51) Int. Cl.
*A61B 17/70* (2006.01)

(52) U.S. Cl.
CPC ...... *A61B 17/7037* (2013.01); *A61B 17/7034* (2013.01); *A61B 17/7035* (2013.01);
(Continued)

(58) Field of Classification Search
CPC ........................................... A61B 17/70–7046
See application file for complete search history.

(56) References Cited

U.S. PATENT DOCUMENTS 5,672,176 A 9/1997 Biedermann et al.
8,353,932 B2 * 1/2013 Jackson ............... A61B 17/702
606/246

(Continued)

FOREIGN PATENT DOCUMENTS

CN 101166478 A 4/2008
CN 103479418 A 1/2014
(Continued)

OTHER PUBLICATIONS

Extended European Search Report for Application No. 18151105.6, dated Jun. 13, 2018, 7 pages.

*Primary Examiner* — Eduardo C Robert
*Assistant Examiner* — Steven J Cotroneo
(74) *Attorney, Agent, or Firm* — Lewis Roca Rothgerber Christie LLP

(57) ABSTRACT

A polyaxial bone anchoring device includes a receiving part with two legs defining a recess for receiving a rod and a pressure member for exerting pressure on a head of a bone anchoring element in the receiving part, the pressure member having an engagement portion. The engagement portion can extend at least partially into a leg and is directly engageable from outside the bone anchoring device to move the engagement portion axially for adjusting the pressure member from a non-locking position where the head is pivotable to a locking position where the head is clamped. When the pressure member is in the locking position and the engagement portion is free from any outside axial forces, a first contact surface of the receiving part cooperates with a
(Continued)

second contact surface of the pressure member to hold the pressure member in the locking position.

22 Claims, 15 Drawing Sheets

Related U.S. Application Data

(60) Provisional application No. 62/615,724, filed on Jan. 10, 2018.

(52) U.S. Cl.
CPC ........ *A61B 17/708* (2013.01); *A61B 17/7085* (2013.01); *A61B 17/7086* (2013.01)

(56) References Cited

U.S. PATENT DOCUMENTS

| | | | |
|---|---|---|---|
| 8,926,671 B2* | 1/2015 | Biedermann | A61B 17/7032 606/268 |
| 9,155,567 B2 | 10/2015 | Auerbach et al. | |
| 9,345,516 B2* | 5/2016 | Biedermann | A61B 17/8605 |
| 10,172,647 B2 | 1/2019 | Elsbury | |
| 10,485,588 B2 | 11/2019 | Jackson | |
| 2007/0270813 A1* | 11/2007 | Garamszegi | A61B 17/7032 606/278 |
| 2007/0288004 A1* | 12/2007 | Alvarez | A61B 17/7032 606/86 A |
| 2008/0269809 A1* | 10/2008 | Garamszegi | A61B 17/8605 606/301 |
| 2009/0326587 A1 | 12/2009 | Matthis et al. | |
| 2010/0331887 A1 | 12/2010 | Jackson et al. | |
| 2011/0160778 A1* | 6/2011 | Elsbury | A61B 17/7037 606/305 |
| 2012/0059426 A1* | 3/2012 | Jackson | A61B 17/7076 606/300 |
| 2012/0143266 A1* | 6/2012 | Jackson | A61B 17/7032 606/328 |
| 2013/0023941 A1* | 1/2013 | Jackson | A61B 17/7038 606/305 |
| 2013/0345761 A1 | 12/2013 | Biedermann et al. | |
| 2014/0107708 A1 | 4/2014 | Biedermann et al. | |
| 2014/0214097 A1 | 7/2014 | Jackson et al. | |
| 2014/0236239 A1* | 8/2014 | Biedermann | A61B 17/7037 606/278 |
| 2015/0032162 A1* | 1/2015 | Biedermann | A61B 17/7035 606/278 |
| 2015/0080960 A1* | 3/2015 | Biedermann | A61B 17/7037 606/279 |
| 2015/0134004 A1 | 5/2015 | Ziolo et al. | |
| 2015/0142060 A1* | 5/2015 | Jackson | A61B 17/7008 606/86 A |
| 2016/0038204 A1 | 2/2016 | Biedermann et al. | |
| 2016/0317206 A1 | 11/2016 | Rezach et al. | |

FOREIGN PATENT DOCUMENTS

| | | |
|---|---|---|
| EP | 3 092 963 A1 | 11/2016 |
| EP | 3 120 791 A1 | 1/2017 |
| WO | 2006/119241 A2 | 11/2006 |
| WO | WO 2012/091737 A1 | 7/2012 |

* cited by examiner

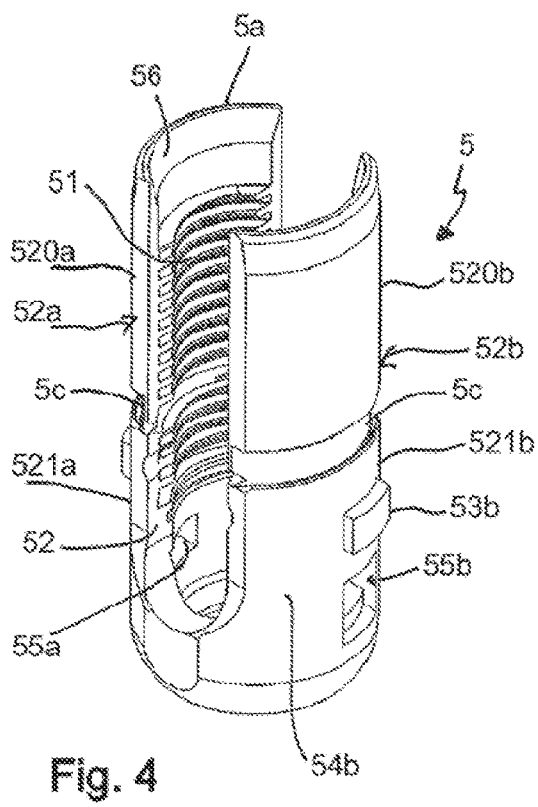 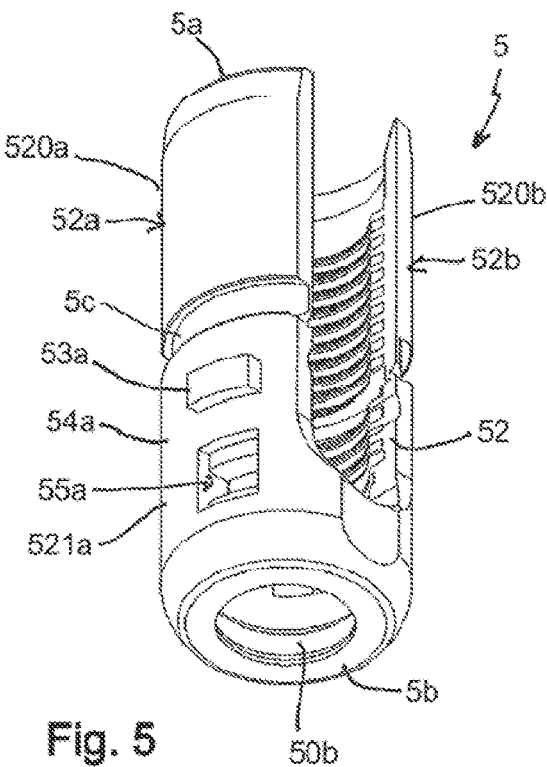
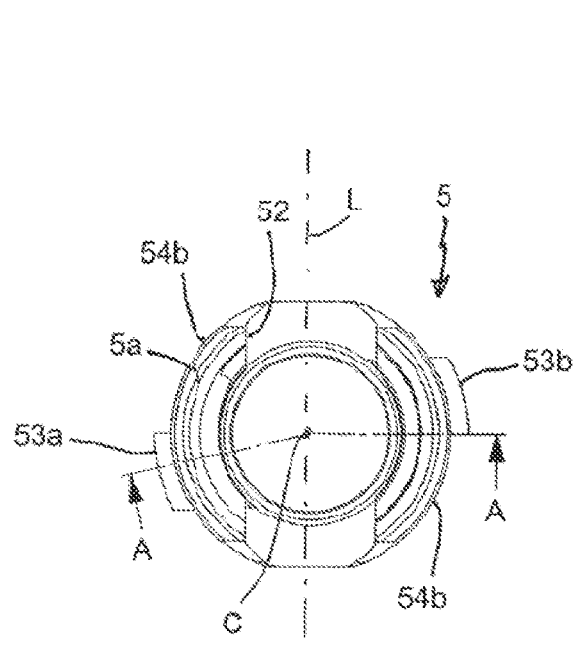 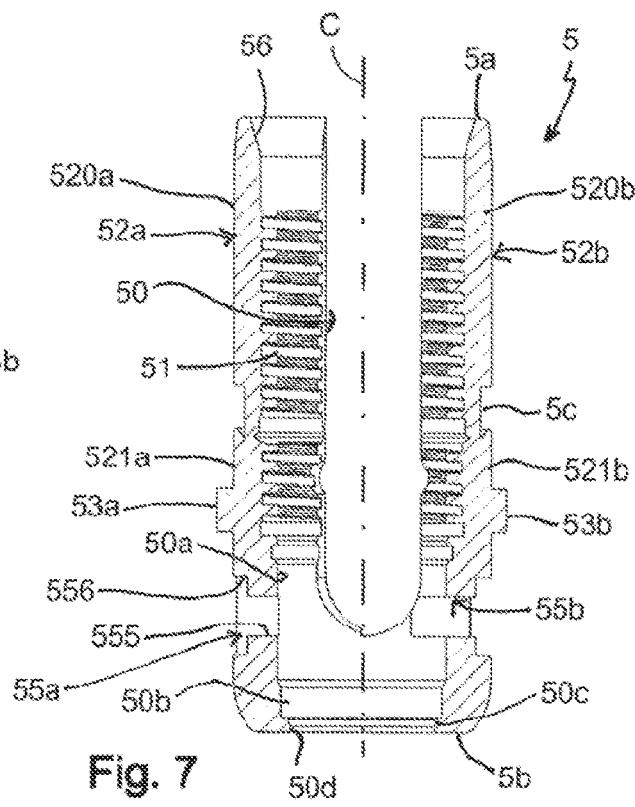
Fig. 4
Fig. 5
Fig. 6
Fig. 7

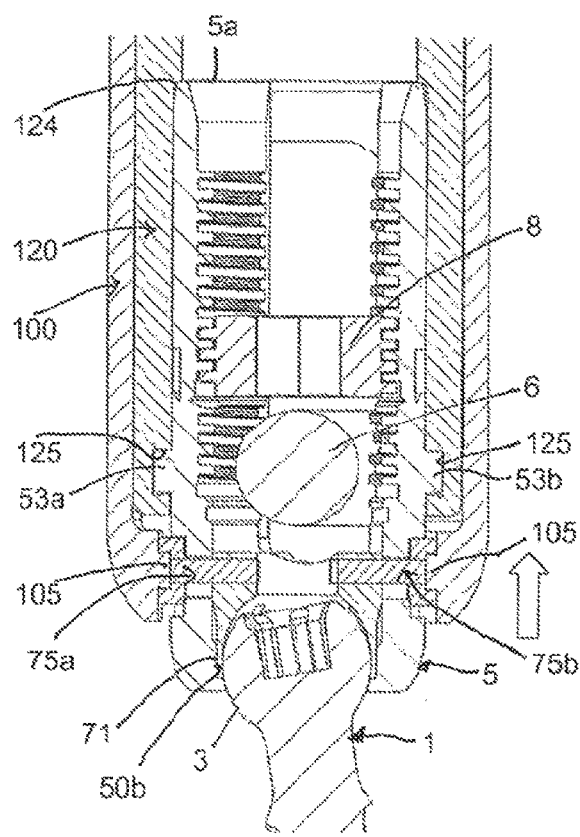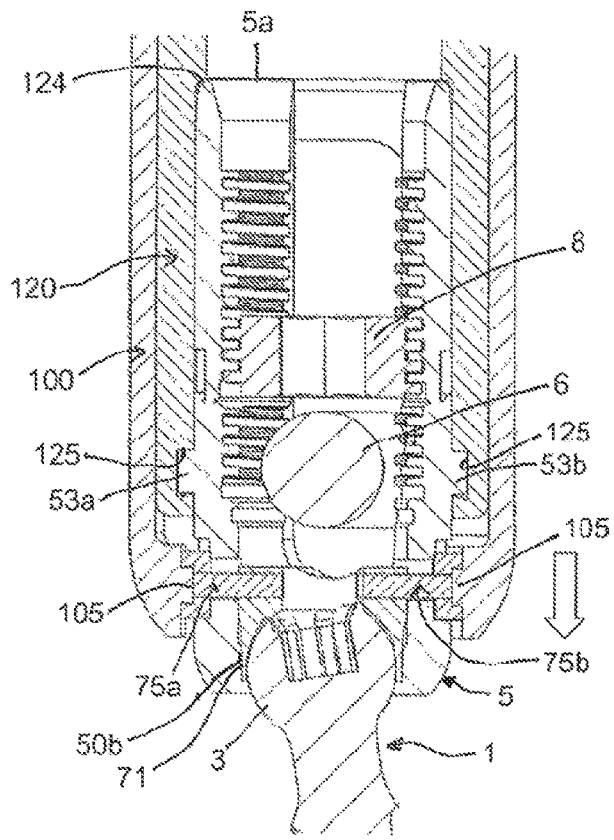
Fig. 16a
Fig. 16b
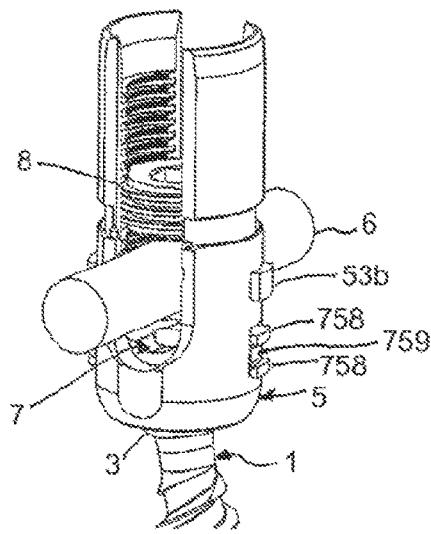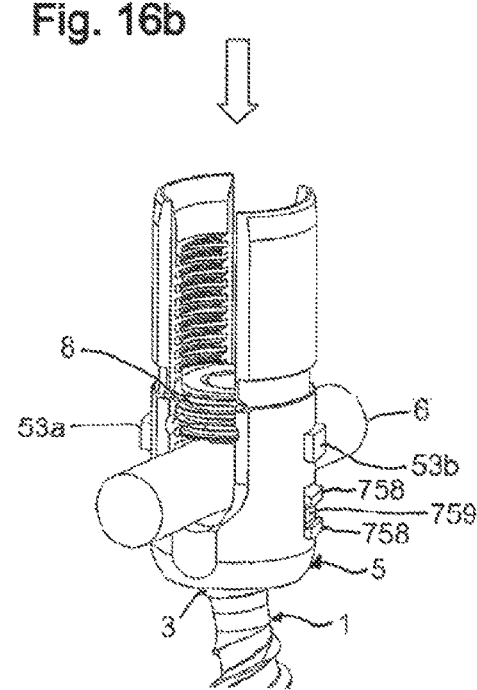
Fig. 17a
Fig. 17b

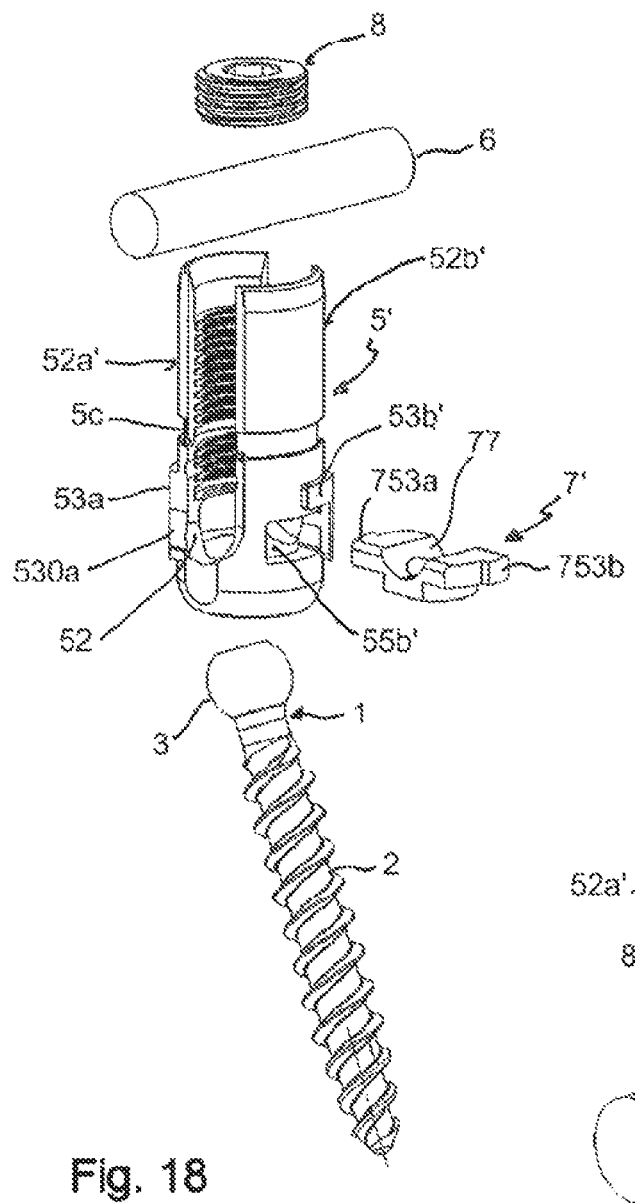
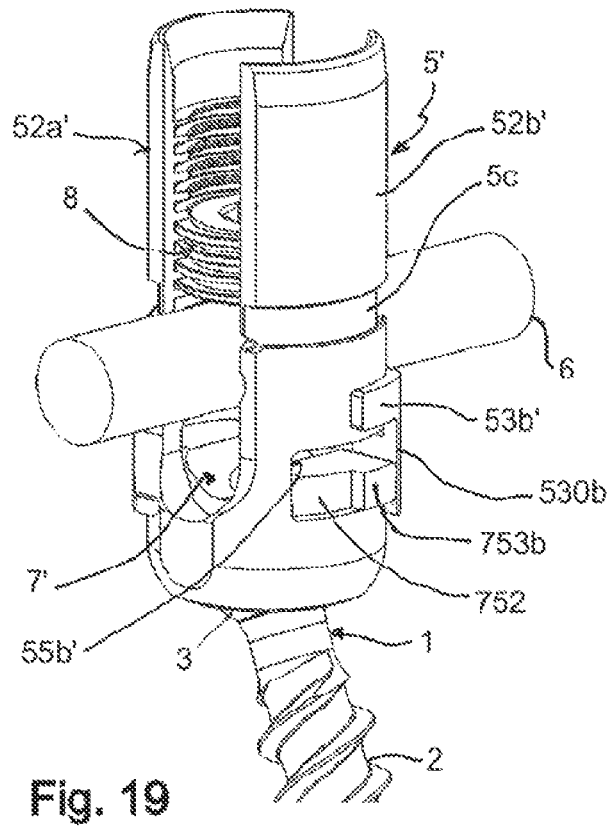
Fig. 18
Fig. 19

POLYAXIAL BONE ANCHORING DEVICE AND SYSTEM INCLUDING AN INSTRUMENT AND A POLYAXIAL BONE ANCHORING DEVICE

CROSS-REFERENCE TO RELATED APPLICATION(S)

This application is a continuation of U.S. patent application Ser. No. 16/243,794, filed Jan. 9, 2019, which claims priority to and the benefit of U.S. Provisional Patent Application No. 62/615,724, filed Jan. 10, 2018, the contents of which are hereby incorporated by reference in their entirety, and claims priority from European Patent Application EP 18 151 105.6, filed Jan. 10, 2018, the contents of which are hereby incorporated by reference in their entirety.

BACKGROUND

The invention relates to a polyaxial bone anchoring device and a system including a polyaxial bone anchoring device and an instrument for use with the device. More specifically, the polyaxial bone anchoring device includes a receiving part configured to assume multiple angular positions with respect to a bone anchoring element for coupling a rod to the bone anchoring element, and a pressure member for exerting pressure onto a head of the bone anchoring element to clamp the head relative to the receiving part, wherein the pressure member can be actuated via the instrument.

DESCRIPTION OF RELATED ART

U.S. Pat. No. 5,672,176 describes an anchoring member for connecting a rod with a bone that includes a screw member with a shank and a head, a seat part receiving the screw head, and the rod. The anchoring member further includes a pressure member that is formed to embrace the screw head from its side opposite to the shank. The seat part has a portion tapering towards a lower end with a predetermined cone angle, and the pressure member has an outer conical surface in the region surrounding the screw head, wherein the conical surface tapers towards the lower end with a cone angle corresponding to the predetermined cone angle. In one embodiment, the cone angle is selected such that self locking occurs between the pressure member and the anchoring member. The head and the rod are locked by tightening a fixation member. The locking of the head remains when the fixation member is loosened to correct the position of the rod.

U.S. Pat. No. 9,155,567 describes a polyaxial pedicle screw including a receiving head having a transversal U-shaped passage, and a shank having a bulging end rotatably housed within the receiving head. The pedicle screw further includes a locking insert housed in the receiving head and mateable with the bulging end. The receiving head comprises a lateral aperture exposing a contact surface of the locking insert in such a way that an external pressing component can act on the contact surface to maintain the locking insert in its locking position.

SUMMARY

In spinal surgery, often multiple segments of the spinal column have to be corrected and/or stabilized using a spinal rod and polyaxial bone anchors. During such a procedure, repeated adjustments of a bone anchoring element and the rod relative to a receiving part of a polyaxial bone anchoring device may become necessary. Therefore, there is a need for more flexibility in the handling of the polyaxial bone anchoring device in terms of locking and unlocking the head and the rod during the correction steps.

It is an object of the invention to provide a polyaxial bone anchoring device that allows for improved handling during surgery, and to provide an instrument adapted for use with such a polyaxial bone anchoring device.

According to an embodiment, a polyaxial bone anchoring device includes a bone anchoring element having a shank for anchoring in bone and a head, a receiving part having a first end and a second end, a central axis extending through the first end and the second end, a recess for receiving a rod, wherein the receiving part receives the head of the bone anchoring element, and a pressure member for exerting pressure onto the head, wherein the pressure member includes at least one engagement portion that is configured to be engaged by an instrument so as to move the pressure member in an axial direction from a non-locking position in which the head is pivotable in the receiving part to a locking position in which the head is clamped, and wherein the receiving part includes a first contact surface that cooperates with a second contact surface at the pressure member in such a manner that the pressure member is configured to remain in the locking position when the instrument is removed.

According to an embodiment, the polyaxial movement of the head relative to the receiving part can be activated and deactivated by moving the pressure member in an axial direction. When the polyaxial movement is deactivated, for example, when the head is temporarily locked, the head remains in this condition even if the instrument is removed. This allows correction steps to be performed without the instrument being attached, and to attach the instrument again if necessary.

Moreover, the head can be locked relative to the receiving part in an angular position and can be unlocked from that angular position independently from the fixation of the rod. Hence, the locking of the head can be maintained while adjustments on the position of the rod can be made. The unlocking of the head can be easily achieved.

Locking and unlocking of the bone anchoring element during surgery can be carried out when the rod and a fixation member are not yet inserted or are positioned at an elevated position in the receiving part, away from a bottom of the rod receiving recess.

According to a further embodiment, the pressure member can be temporarily held in the locking position by friction, for example through a press-fit connection between the pressure member and the receiving part. The strength of the holding force can be adjusted by selecting the size of the cooperating parts.

By the recess for the rod, two legs may be defined, each of which may include a separable portion that forms extended tabs. The extended tabs allow convenient manipulation of the polyaxial bone anchoring device during surgery. Furthermore, the extended tabs permit guiding and/or supplying elements of an implant or instruments to the implantation site. This is particularly useful in the case of minimally invasive surgery (MIS). The extended tabs may be broken off after locking the head and the rod.

When the head of the bone anchoring element is temporarily locked in the receiving part and the rod is still movable, it is possible to pull the bone anchoring device with the instrument towards the inserted rod, thereby also pulling the associated vertebra towards the rod for correcting a position of the vertebra. Therefore, the polyaxial bone anchoring device permits various adjustments and re-adjustments of the angular position and/or rod position during surgery.

According to embodiments, the polyaxial bone anchoring device can be designed as a top loading bone anchoring device, wherein the bone anchoring element is inserted into the receiving part from a top end thereof, or as a bottom loading bone anchoring device wherein the bone anchoring element is inserted into the receiving part from a bottom end thereof. The latter permits insertion of the bone anchoring element in the bone first, and thereafter mounting the receiving part with the pressure member onto the head of the bone anchoring element.

BRIEF DESCRIPTION OF THE DRAWINGS

Further features and advantages of the invention will become apparent from the description of embodiments by means of the accompanying drawings. In the drawings:

FIG. 4 shows a perspective view from a top of a receiving part of the polyaxial bone anchoring device of FIGS. 1 to 3.

FIG. 5 shows a perspective view from a bottom of the receiving part of FIG. 4.

FIG. 6 shows a top view of the receiving part of FIGS. 4 and 5.

FIG. 7 shows a cross-sectional view of the receiving part of FIGS. 4 to 6, the cross-section taken along line A-A in FIG. 6.

FIGS. 16a and 16b show cross-sectional views of unlocking and locking a head of a bone anchoring element in the polyaxial bone anchoring device of FIGS. 1 to 12 using the instrument of FIGS. 13 and 14.

FIGS. 17a and 17b show perspective views of steps of inserting and locking a rod to the polyaxial bone anchoring device of FIGS. 1 to 12.

FIG. 18 shows an exploded perspective view of another embodiment of a polyaxial bone anchoring device.

FIG. 19 shows a perspective view of the polyaxial bone anchoring device of FIG. 18 in an assembled state.

FIG. 32b shows an enlarged view of a detail of FIG. 32a.

FIG. 33b shows an enlarged view of a detail of FIG. 33a.

DETAILED DESCRIPTION

Figure 1:
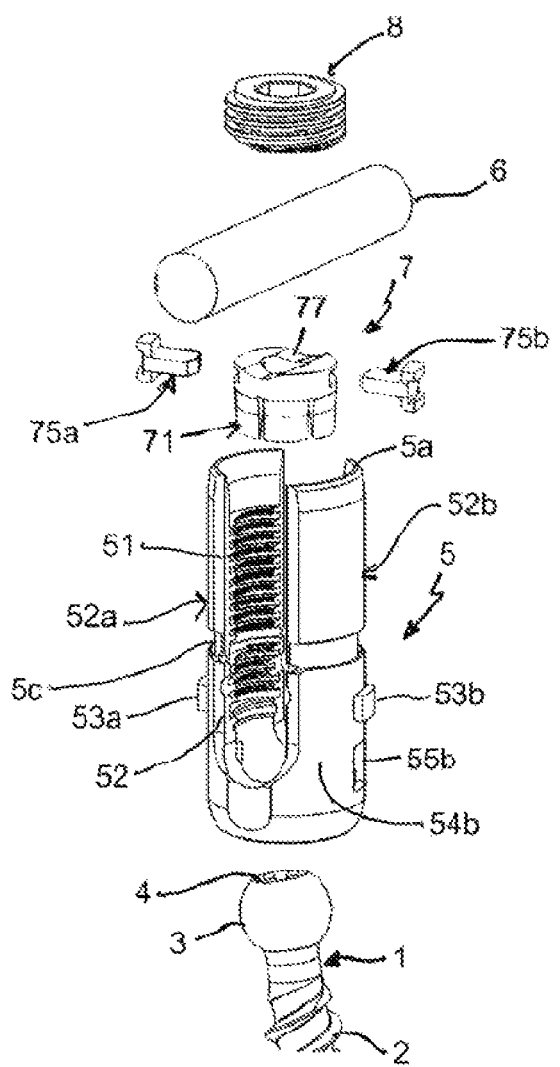
FIG. 1 shows an exploded perspective view of an embodiment of a polyaxial bone anchoring device.
Figure 2:
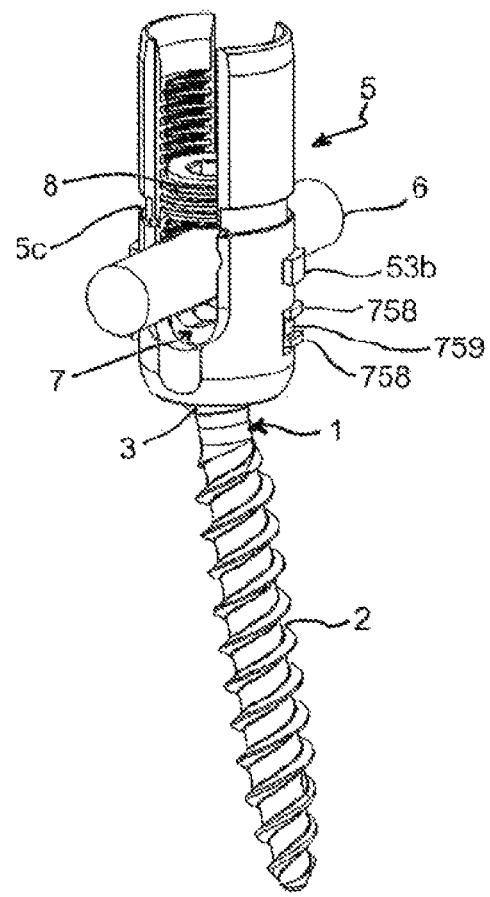
FIG. 2 shows a perspective view of the polyaxial bone anchoring device of FIG. 1 in an assembled state.
Figure 3:
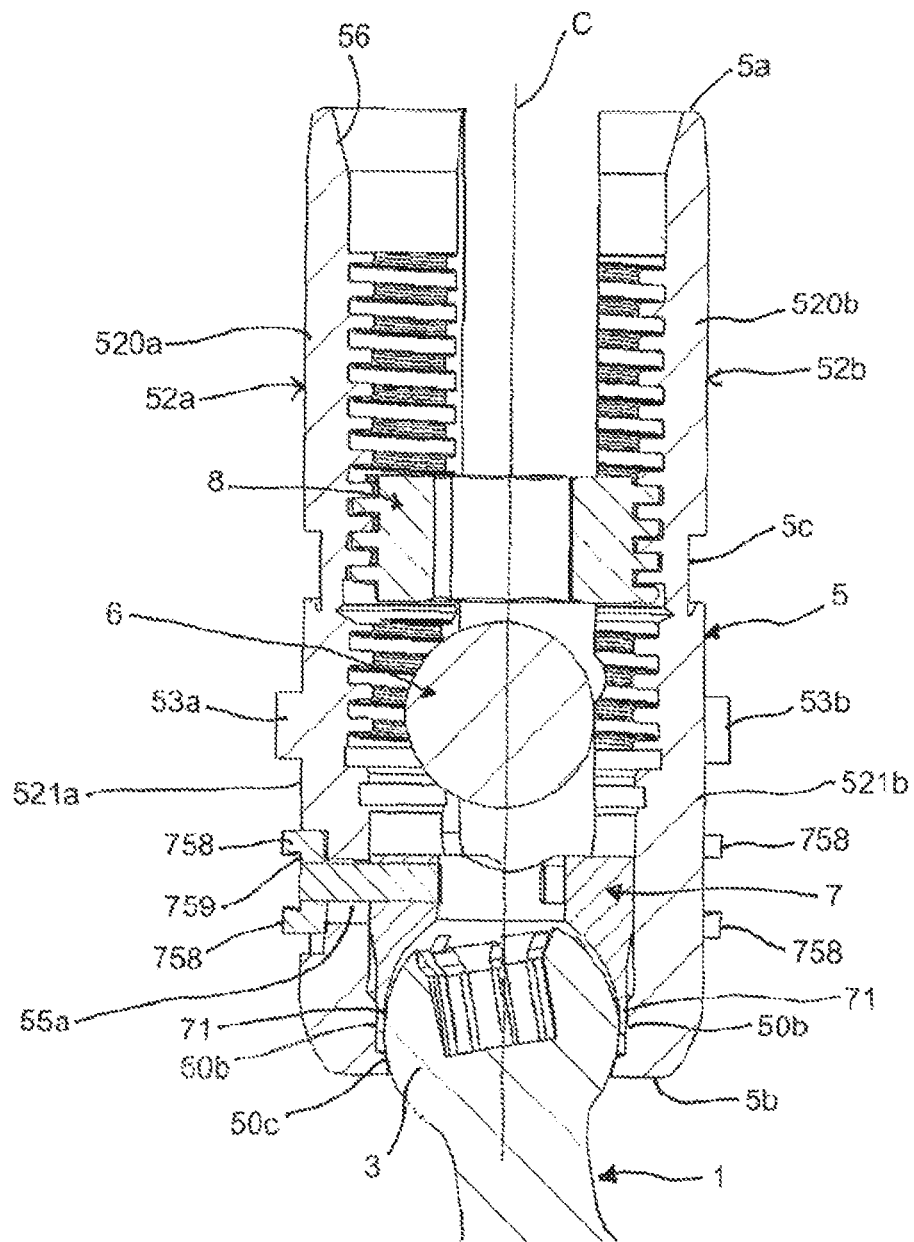
FIG. 3 shows a cross-sectional view of the polyaxial bone anchoring device of FIGS. 1 and 2 in an assembled state, wherein the cross-section is taken in different longitudinal planes for the right side and the left side.
Figure 8:
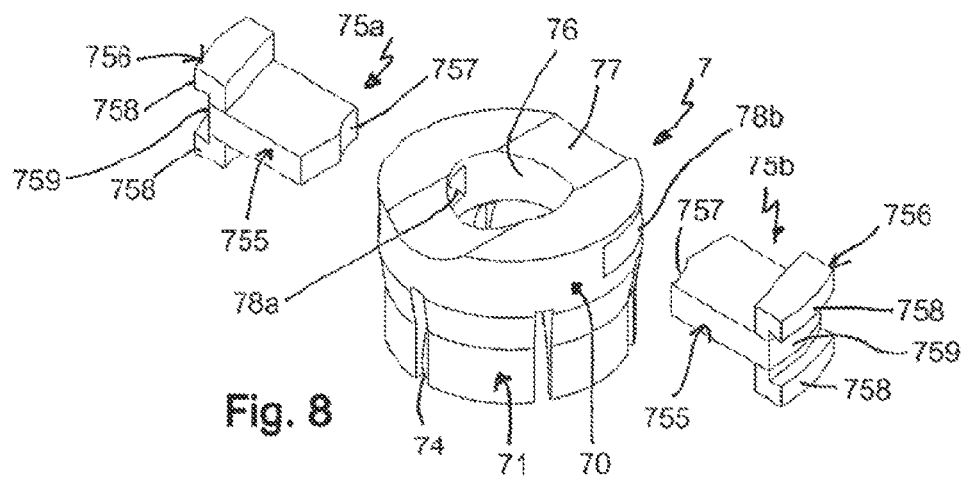
FIG. 8 shows a perspective exploded view of a pressure member of the polyaxial bone anchoring device of FIGS. 1 to 3.
Figure 9:
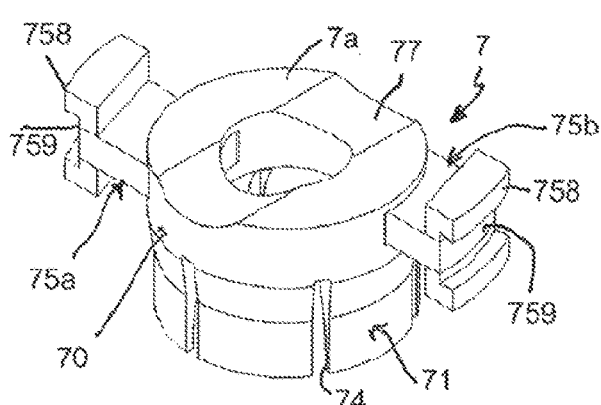
FIG. 9 shows a perspective view from a top of the pressure member of FIG. 8.
Figure 10:
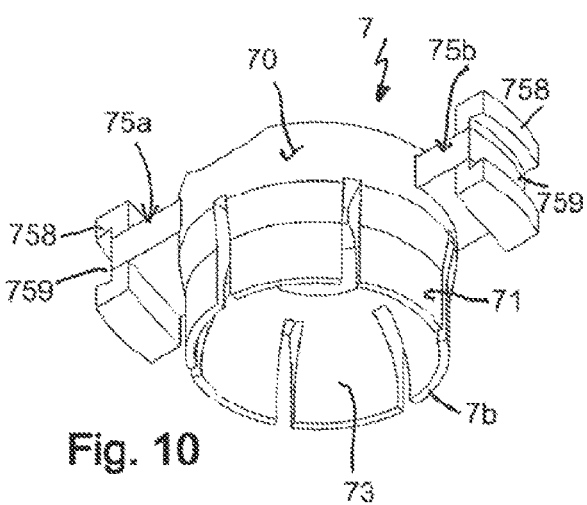
FIG. 10 shows a perspective view from a bottom of the pressure member of FIG. 9.

As depicted in FIGS. 1 to 3, a bone anchoring device according to an embodiment of the invention includes a bone anchoring element 1 in the form of, for example, a bone screw having a shank 2 with a threaded portion and a head 3 with a spherically-shaped outer surface portion. The head 3 may have a recess 4 for engagement with a driver. The bone anchoring device also includes a receiving part 5 for receiving a rod 6 to be connected to the bone anchoring element 1. In addition, a pressure member 7 may be provided in the receiving part 5 for exerting pressure onto the head 3 of the bone anchoring element 1. Lastly, the bone anchoring device also includes a fixation member 8, in the form of, for example, an inner screw or set screw for fixing the rod in the receiving part 5.

The receiving part 5 will be described in greater detail, referring additionally to FIGS. 4 to 7. The receiving part 5 includes a first end 5a forming an upper end and an opposite second end 5b forming a lower end, and a central axis C that passes through the first end 5a and the second end 5b. The overall outer shape of the receiving part may be substantially cylindrical. A passage 50 extends through the receiving part 5 from the first end 5a to the second end 5b. The passage 50 may have several sections having different diameters. In one section that starts at or close to the first end 5a and extends to a distance from the first end 5a, the passage 50 is formed as a first coaxial bore 50a that may be provided at least in a portion thereof with an internal thread 51. The passage 50 further may narrow into a second coaxial bore 50b having a smaller diameter than the first coaxial bore 50a. The second coaxial bore 50b may serve for accommodating a portion of the pressure member 7 therein. An inner surface of the second coaxial bore 50b defines a first contact surface for cooperating with a second contact surface provided on the pressure member 7. Between the second end 5b and the second coaxial bore 50b, a seat 50c for the head is formed that may be spherically-shaped or otherwise shaped to allow a pivoting motion of an inserted head similar to a ball and socket joint. A narrowing portion 50d may further be located between the second end and the seat 50c, so that the opening at the second end 5b permits passing of the shank 2 therethrough, but not the head 3. The second coaxial bore 50b is shown to be cylindrical, but can also be conical or otherwise shaped to allow a frictional connection, preferably a press-fit connection, with a portion of the pressure member 7.

In an upper region of the receiving part 5, a recess 52 that may be substantially U-shaped extends from the first end 5a in the direction of the second end 5b, wherein a width of the recess 52 is slightly larger than a diameter of the rod 6, such that the rod 6 can be placed in the recess 52 and can be guided therein. By means of this, the recess 52 forms a rod receiving recess or a channel for the rod 6, wherein the sidewalls of the channel define two free legs 52a, 52b.

At a distance from the first end 5a, a break-away or break-off portion in the form of a circumferential groove 5c is arranged that permits breaking off of a portion of the legs 52a, 52b above the groove 5c. The groove divides the legs 52a, 52b into a first or upper portion 520a, 520b extending above the groove 5c and a second or lower portion 521a, 521b extending below the groove 5c to a base of the recess 52. At the groove 5c, a wall thickness of the legs 52a, 52b may be reduced to enable breaking away of the upper portion 520a, 520b of the legs. By means of this, the upper portion 520a, 520b, respectively, form extended tabs that may be used as guiding means for guiding instruments or implant parts to a lower region of the bone anchoring device. Such extended tabs may be particularly suitable for minimally invasive surgery (MIS). Any other means for permitting breaking away of the upper portion 520a, 520b from the lower portion 521a, 521b may be contemplated, such as, for example, perforations, etc. The internal thread 51 is provided along at least a portion of the upper portion 520a, 520b and at least a portion of the lower portion 521a, 521b of the legs 52a, 52b, so that the fixation member 8 can be screwed down along the pathway defined by the first coaxial bore 50a.

At the outer surface of the receiving part 5, an engagement structure for engagement with the instrument is arranged, wherein the engagement structure may be formed by circumferential ribs or protrusions 53a, 53b. In the embodiment shown, on each leg 52a, 52b there is one rib 53a, 53b. The ribs 53a, 53b are preferably positioned on the lower portion 521a, 521b of the legs 52a, 52b, below the groove 5c, respectively. Each of the ribs 53a, 53b extends along a segment of the circumference of the receiving part. The arrangement of the ribs 53a, 53b is axially or rotationally symmetrical with respect to the central axis C, or asymmetric, specifically non mirror-symmetrical, with respect to a plane extending through the central axis C and a longitudinal axis L of the recess 52. More specifically, the ribs 53a, 53b are offset from one another by 180° measured in relation to the central axis C, and are rotated with respect to the central axis C such that one rib 53a is closer to a first end of the recess 52 in a circumferential direction and the other rib 53b is closer to the second end of the recess 52. Thus, in a circumferential direction, there is a rib-free surface portion 54a, 54b on the outer surface of each leg 52a, 52b. This permits the instrument to be placed first onto the rib-free portions 54a, 54b and then to be rotated to engage the ribs 53a, 53b, as described in greater detail below. The ribs 53a, 53b may have a substantially rectangular cross-section or any other cross-section that facilitates engagement by the instrument. It shall be understood that the number of ribs on each leg 52a, 52b is not limited to one single rib, for example, more than two ribs may be provided on each leg in other embodiments. Also the shape of the ribs may be different in other embodiments.

The receiving part 5 further includes two apertures 55a, 55b for permitting the instrument to engage the pressure member 7. The apertures 55a, 55b are arranged laterally with respect to the central axis C and with respect to the longitudinal axis L of the recess 52. Each aperture 55a, 55b extends fully through the wall of the receiving part 5. More in detail, the apertures are located in the lower portion 521a, 521b of the legs 52a, 52b, respectively, and between the engagement portions in the form of the ribs 53a, 53b and the second end 5b. Hence, the apertures 55a, 55b are also arranged axially or rotationally symmetrical with respect to the central axis C, or asymmetrically (non mirror-symmetrical) with respect to a plane extending through the central axis C and the longitudinal axis L of the recess 52. Preferably a position of a center of the aperture 55a, 55b corresponds in a circumferential direction to a position of a center of the associated rib 53a, 53b, and a circumferential width of the aperture corresponds substantially to a circumferential width of the associated rib.

As explained more in detail with reference to FIG. 7, each aperture 55a, 55b has an inner portion 555 open to the first coaxial bore 50a and having a width in a circumferential direction that is greater than its height in an axial direction. Additionally, each aperture 55a, 55b has an outer portion 556 with a height in the axial direction that is greater than the height of the inner portion 555.

Lastly, adjacent to the first end 5a of the receiving part 5, a tapered thread-free portion 56 may be provided, wherein the taper widens towards the first end 5a, to facilitate insertion of the pressure member 7. Moreover, the internal thread 51 may start at a distance from the tapered portion 56.

The pressure member 7 will be described in more detail, referring additionally to FIGS. 8 to 12. The pressure member 7 includes a first end 7a forming an upper end and a second end 7b forming a lower end. Adjacent to the first end, the pressure member has a first portion 70 with a substantially cylindrical outer surface, wherein the first portion 70 is configured to be slidably movable in the first coaxial bore 50a of the receiving part 5. Adjacent to the second end 7b, a second portion 71 is provided that has a substantially cylindrical outer surface defining a second contact surface that is configured to cooperate with the first contact surface at the second coaxial bore 50b of the receiving part. The size of the second portion 71 of the pressure member 7 and of the second coaxial bore 50b in the receiving part is such that the second portion 71 is held in a press-fit manner when the head 3 is in the receiving part and the pressure member 7 is in a lowermost position. A tapered transition portion 72 may connect the first portion 70 and the second portion 71.

A hollow interior chamber 73 extends through the second portion 72, preferably up to the first portion 71, and provides an opening at the second end 7b. The interior chamber 73 is configured to accommodate and clamp the spherical head 3 therein. To achieve this, the second portion 72 is at least partially flexible by means of slits 74 that are open towards the second end 7b and that extend preferably through the entire or most of the second portion 72. The number and dimensions of the slits 74 are such that the wall of the second portion is flexible enough to snap onto the head 3.

The pressure member 7 further includes two lateral extensions for engagement with the instrument. The lateral extensions are designed as pins 75a, 75b that are separate parts and that can be mounted to the pressure member after the pressure member has been inserted into the receiving part 5. For mounting the pins 75a, 75b, the first portion 70 has openings 78a, 78b that are adapted to receive an end portion of the pins therein. Each pin 75a, 75b has an inner portion 755 and an outer portion 756, wherein the inner portion is adapted to be received in the inner portion 555 of the aperture 55a, 55b, and the outer portion is adapted to be received at least partially in the outer portion 556 of the aperture 55a, 55b, respectively. The inner portion 755 is substantially flat with a height that is smaller than the height of the apertures 55a, 55b in the axial direction, so that the pins 75a, 75b can move in the apertures 55a, 55b in the axial direction, respectively. At the inner free end, a cylindrical cut-out portion 757 is located that is adapted to the cylindrical shape of a coaxial bore 76 provided in the pressure member 7 for accessing the head 3. The second portion 756 has two axially spaced apart ribs 758 separated by a groove 759, for example, with a dovetail cross-section, that form engagement portions for the instrument. As can be seen in particular in FIG. 3, when the pressure member 7 is inserted into the receiving part 5, and the pins 75a, 75b are mounted, the ribs 758 protrude at least partially out of the apertures 55a, 55b.

Figure 11:
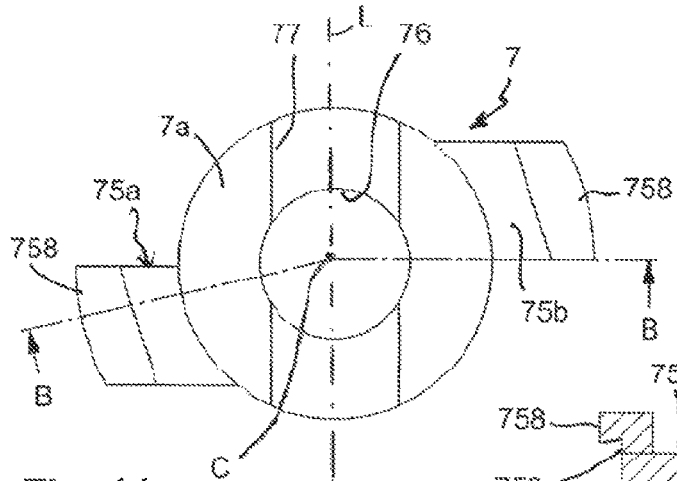
FIG. 11 shows a top view of the pressure member of FIGS. 8 to 10.
Figure 12:
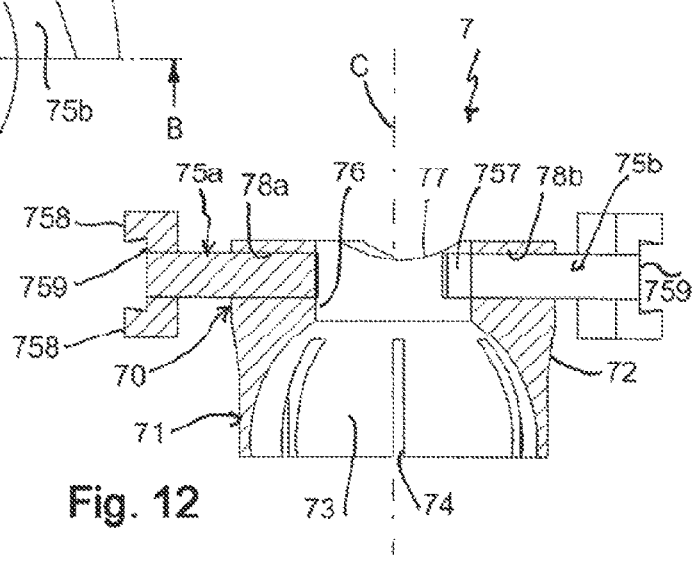
FIG. 12 shows a cross-sectional view of the pressure member of FIGS. 8 to 11, the cross-section taken along line B-B in FIG. 11.

As shown in particular in FIG. 11, in a top view the pins 75a, 75b are oblique and arranged axially or rotationally symmetrical with respect to the central axis C, or asymmetrically with respect to a plane extending through the central axis C and the longitudinal axis L of the recess 52. Hence, the arrangement and shape of the pins 75a, 75b is adapted to the arrangement and shape of the apertures 55a, 55b.

Moreover, the pressure member has a rod support surface 77 on the first portion 70 configured to support an inserted rod 6. The rod support surface 77 may have a cylindrical shape adapted to the shape of the rod 6.

Figure 13:
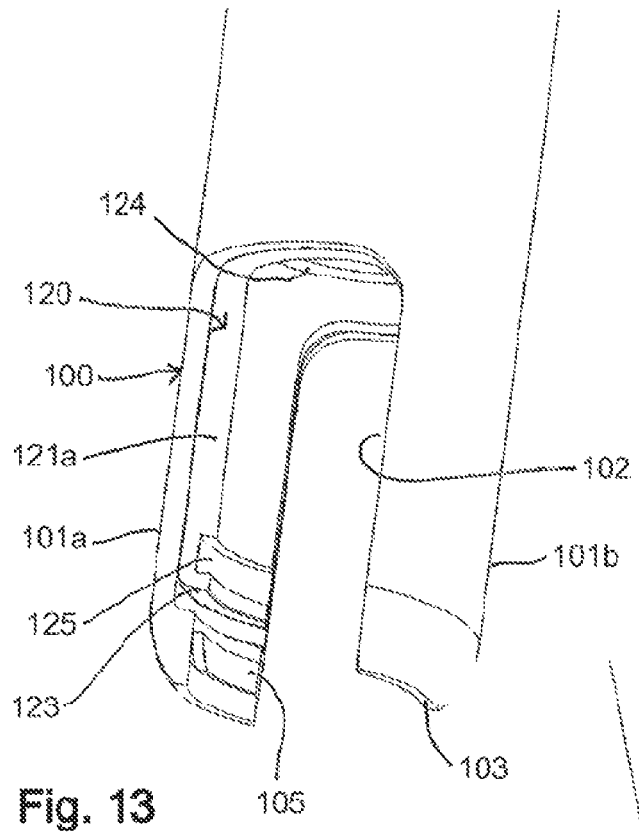
FIG. 13 shows a perspective view from a side of a front portion of an instrument for use with the polyaxial bone anchoring device according to FIGS. 1 to 12.
Figure 14:
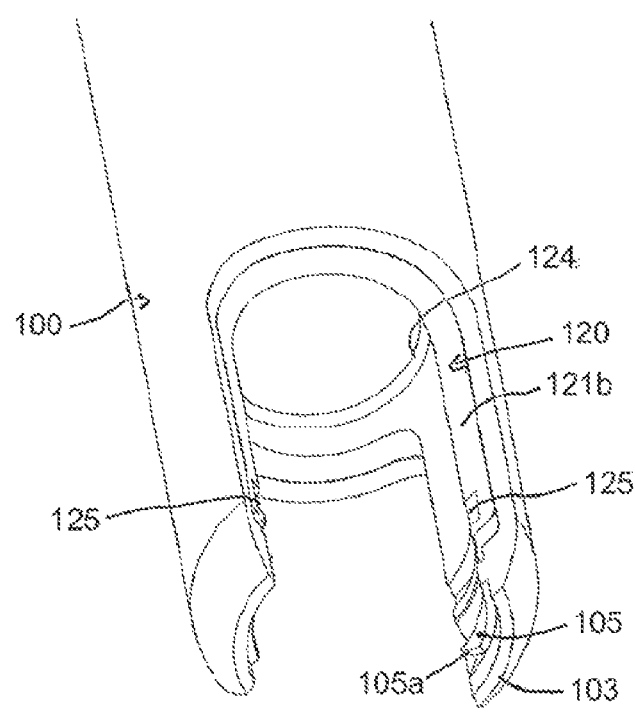
FIG. 14 shows a perspective view from a bottom of the front portion of the instrument of FIG. 13.

Turning now to FIGS. 13 and 14, an instrument adapted for use with the polyaxial bone anchoring device will be described. The instrument has an outer tube 100 and an inner tube 120 slideably arranged within the outer tube 100. In the figures, only front portions of the outer tube 100 and the inner tube 120 are shown. Each of the outer tube 100 and the inner tube 120 has a rear portion that may have any suitable shape, in particular, that may have any grip or handle portions to hold and/or move the outer tube 100 relative to the inner tube 120. The displacement of the outer tube relative to the inner tube may be effected, for example, by a toggle lever construction, wherein a first end of the first lever arm is connected to the outer tube 100 and a first end of a second lever arm is connected to the inner tube 120, and wherein second ends of the lever arms can be actuated by hand. Other mechanisms for displacing the outer tube relative to the inner tube may be applied. Preferably the outer tube 100 and the inner tube 120 are slideable with respect to each other in a guided manner, for example, by protrusions guided in recesses or slots.

The front portion of the instrument is bifurcated. That means the outer tube 100 has two opposite arms 101a, 101b and the inner tube 120 also has two opposite arms 121a, 121b, separated by a substantially U-shaped slot 102. The open side of the slot 102 is directed towards the free ends 103 of the outer tube, i.e., towards the free end of the instrument. A width of the recess 102 is at least as large as an outer diameter of the receiving part 5 in the region of the rib-free surfaces 54a, 54b, such that the instrument can be placed onto and around the receiving part 5. A length of the recess 102 in an axial direction is such that the receiving part 5 can be accommodated in the front portion of the tubes 100, 120. Thus, the inserted rod 6 can also extend through the recess 102. Close to a free end 123 of the inner tube 120, a circumferential groove 125 is provided on each of the arms 121a, 121b. The groove 125 is configured to engage the engagement portions in the form of the ribs 53a, 53b at the outer surface of the receiving part 5. Similarly, at a distance from the free end 103 of the outer tube 100, an engagement portion in the form of a protrusion 105 is formed that is configured to engage the groove 759 between the ribs 758 of the pins 75a, 75b, respectively. The protrusion 105 may have in a circumferential direction at one side an inclined portion 105a to facilitate the engagement with the groove 759. The inclined portion 105a may be provided at the side that engages the groove 759 first during a rotational movement of the instrument, as explained below.

A shoulder 124 may be formed at the inner tube 120 at a distance from the free end 123, that is configured to abut against the first end 5a of the receiving part 5 when the instrument is attached. As can be seen further in the figures, an inner diameter of the inner tube 120 above the shoulder 124 is such that the fixation member 8 can be inserted through the inner tube 120 into the receiving part 5.

The receiving part 5, the pressure member 7, the fixation member 8, and the bone anchoring element 1, as well as the rod 6 and the instrument, may each be made of bio-compatible materials, for example of Titanium or stainless steel, of a bio-compatible alloy, such as NiTi-alloys, for example Nitinol, of magnesium or magnesium alloys, or from a bio-compatible plastic material, such as, for example, polyether ether ketone (PEEK) or poly-l-lactide acid (PLLA). In addition, the parts can be made of the same or of different materials from one another.

The polyaxial bone anchoring device is assembled as follows. First, the bone anchoring element 1 is inserted from the first end 5a into the receiving part until the shank 2 extends through the opening at the second end 5b and the head 3 rests in the seat 50c. Then the pressure member 7 is inserted through the first end 5a until the openings 78a, 78b are accessible through the apertures 55a, 55b, respectively. Thereby the rod support surface 77 is aligned with the U-shaped recess 52 of the receiving part. Thereafter, the pins 75a, 75b are mounted through the apertures 55a, 55b of the receiving part until they extend through the openings 78a, 78b and held therein, for example via a press-fit connection. The second portion 71 extends into the second coaxial bore 50b and around the inserted head 3. As shown in FIGS. 3 and 16a, when the pins 75a, 75b are in an uppermost position and abut against an upper edge of the apertures 55a, 55b, the pressure member does not extend fully into the second coaxial bore 50b. This is a non-locking position of the pressure member 7. In the non-locking position the head is pivotable with respect to the receiving part 5.

The pressure member is configured to lock the head in a locking position (e.g., as shown in FIG. 16b), where the second portion 71 is moved further downward and into the second coaxial bore 50b where it is pressed by the head 3 against the inner wall of the second coaxial bore 50b to achieve a press-fit connection between the pressure member 7 and the receiving part 5. This is the locking position of the pressure member 7. The locking position may be defined by the pins 75a, 75b abutting against a lower edge of the apertures 55a, 55b, respectively.

Figure 15A:
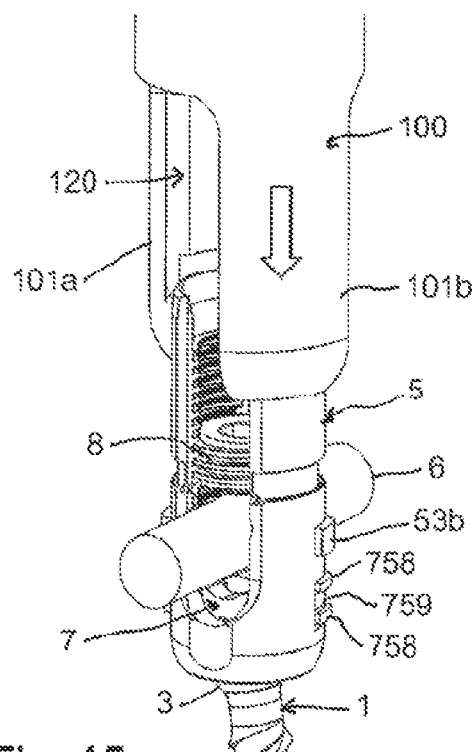
FIGS. 15a to 15d show perspective views of steps of use of the instrument of FIGS. 13 and 14 with the polyaxial bone anchoring device of FIGS. 1 to 12.

FIGS. 15a to 15d depict steps of placing the instrument onto the receiving part 5. The bone anchoring element 1 may already be inserted into a bone or a vertebra and the pressure member 7 is mounted into the receiving part. The rod 6 and the fixation member 8 may already be inserted and the fixation member 8 may not be tightened, so that the rod 6 is still movable along the rod axis and also has some space for moving axially up and down. The front portion of the instrument is oriented such that the legs 101a, 101b, 121a, 121b are aligned with the rib-free surface portions 54a, 54b of the receiving part 5, as shown in FIG. 15a.

Figure 15B:
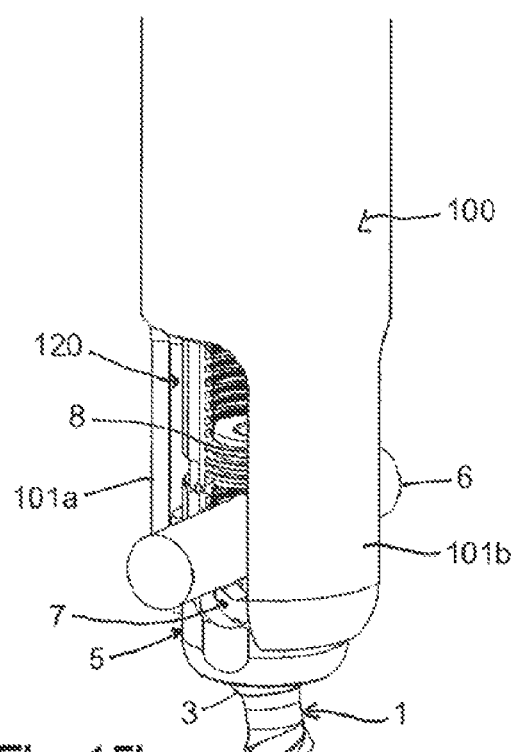

Then, as shown in FIG. 15b, the instrument is moved downward relative to the receiving part 5, so that the legs are placed over the rib-free portions 54a, 54b of the receiving part 5 until the first end 5a of the receiving part abuts against the inner shoulder 124 of the inner tube 120. In this position, the grooves 125 of the inner tube 120 are at a same axial position as the ribs 53a, 53b of the receiving part 5 and the protrusions 105 of the outer tube 100 are at a same axial position as the groove between the ribs 758 of the pins 75a, 75b of the pressure member 5. Therefore, when the instrument is rotated as shown in FIG. 15c, the grooves 125 of the inner tube 120 engage the ribs 53a, 53b of the receiving part and at the same time, the protrusions 105 of the outer tube 100 engage the groove 759 of the pins 75a, 75b.

The cooperation of the engagement structures in the form of protrusions and grooves connects the outer tube 100 to the pressure member 7 and the inner tube 120 to the receiving part 5 in a form-fit manner, respectively, such that a force for moving the pressure member 7 relative to the receiving part 5 in an axial direction can be transmitted through the instrument. In FIG. 15d, a downward movement of the outer tube 100 relative to the inner tube 120 is shown that moves the pressure member 7 into the locking position.

FIGS. 16a and 16b show the use of the instrument for locking and unlocking of the head 3. The inner tube 120 is fixed to the receiving part 5. In FIG. 16a the outer tube is pulled upwards relative to the inner tube thereby moving the pressure member via the pins 75a, 75b into the non-locking position where the pins abut against the upper edge of the apertures 55a, 55b. In FIG. 16b, the outer tube 100 is moved downward relative to the inner tube 120 to move the pressure member into the locking position where the pins 75a, 75b abut against the lower edge of the apertures 55a, 55b. Thereby, the second portion 71 of the pressure member 7 is pressed into the second coaxial bore 50b so that the head 3 is firmly clamped or even locked. It shall be noted that an intermediate position of the pressure member may be possible, with a clamping or locking force that is between the respective clamping or locking forces in the non-locking and the locking positions.

Figure 15C:
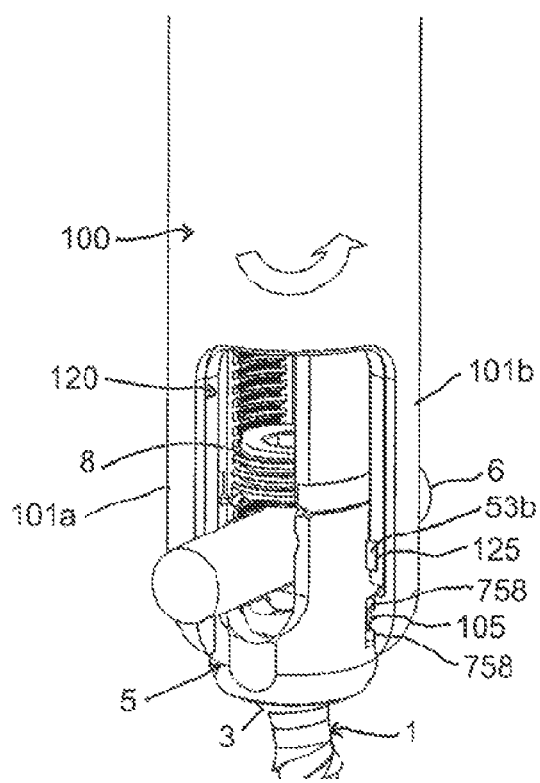
Figure 15D:
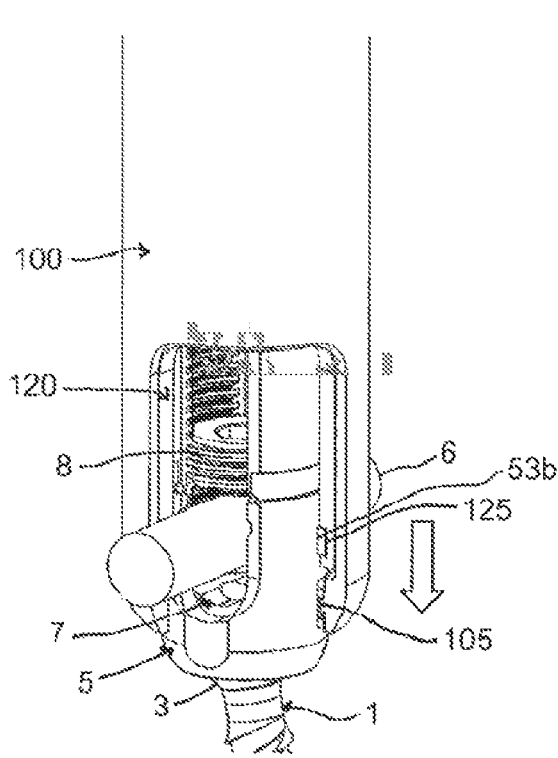
Figure 20:
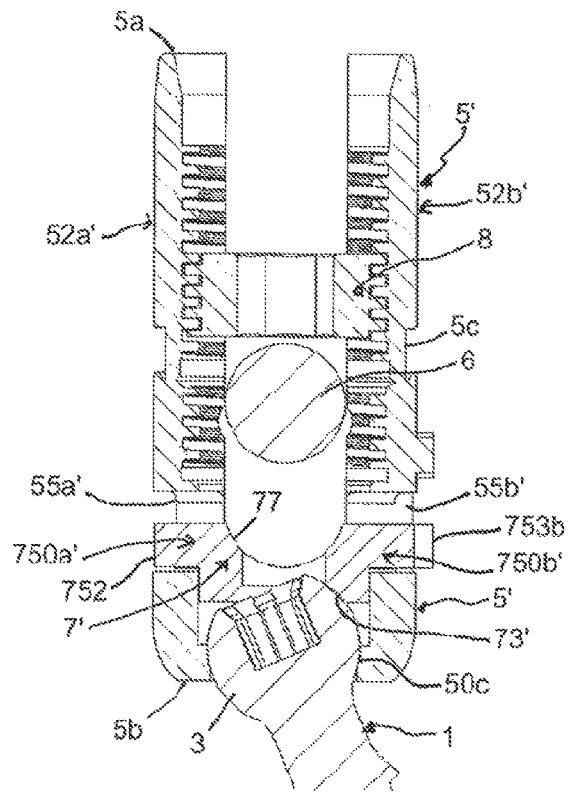
FIG. 20 shows a cross-sectional view of the polyaxial bone anchoring device of FIGS. 18 and 19 in an assembled state, wherein the cross-section is taken in a plane perpendicular to the rod axis and extending through a central axis and through a middle of legs of the receiving part.

Next, as shown in FIG. 17a, when the instrument has been removed by rotating it in the opposite direction of that shown in FIG. 15c, the pressure member 7 remains in the locking position. The rod 6 is still movable which allows re-adjustments of the rod position to be performed. Finally, as shown in FIG. 17b, the fixation member 8 is tightened to fix the rod 6 and to exert additional pressure via the rod 6 onto the pressure member to lock the head and the rod altogether.

The head can be locked and unlocked via the instrument, and remains in the locked position once it has been locked, even after removal of the instrument. Thus, several correction steps can be carried out during surgery, with the advantage that the head remains locked once the pressure member 7 is in the locking position. Thereby, a greater variety of adjustment steps can be carried out, which simplifies the surgical procedure. For example, the polyaxial bone anchoring device can be used in a similar manner as a polyaxial bone anchoring device with a two-part fixation member that provides independent rod and head fixation, wherein, for example, an inner fixation member is used to fix the rod and an outer fixation member is used to lock the head independently from the rod.

In another manner of use, the polyaxial bone anchoring device can be used as a monoaxial bone anchoring device in that the head is locked relative to the receiving part 5, and only adjustments of the rod positions are made.

Furthermore, in the locking position of the pressure member 7, the bone anchoring device can be pulled against the rod, and the position of a vertebra can be corrected.

In a surgical operation, a plurality of bone anchoring devices are connected by the rod 6. It may be possible to use several instruments for several bone anchoring devices simultaneously, which facilitates steps such as adjustments, re-positioning, etc., of each bone anchoring device relative to the rod.

Referring to FIGS. 18 to 33b, a further embodiment of the polyaxial bone anchoring device will be described. The same or similar parts will be described with the same reference numerals, and the descriptions thereof will not be repeated. The polyaxial bone anchoring device according to this embodiment differs from the previously described polyaxial bone anchoring device in the design of the receiving part and the pressure member. The pressure member 7' is a monolithic part and is insertable into the receiving part 5' laterally through lateral apertures 55a', 55b'.

First, as illustrated more in detail in FIGS. 23 to 27, the receiving part 5' has a first coaxial bore 50a' that is followed by the seat 50c. Between the first coaxial bore 50a' and the seat 50c, there may be a step 50e, whereby the coaxial bore may have an increased width compared to the seat 50c. In this embodiment, the receiving part 5' lacks a second coaxial bore for cooperating with the pressure member (e.g., as seen in the first embodiment in FIGS. 1 to 12).

Figure 32A:
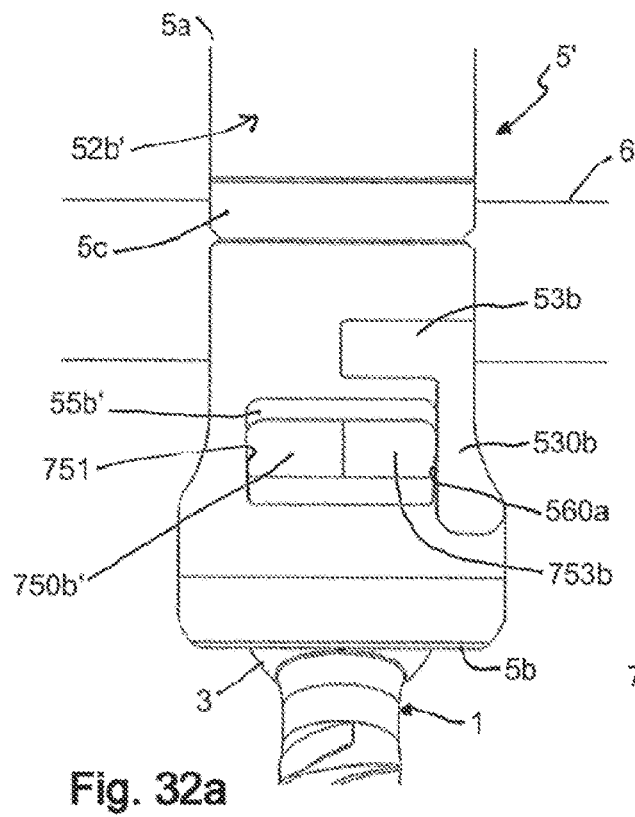
FIG. 32a shows a side view of the polyaxial bone anchoring device of FIGS. 18 to 31 in a non-locking position of the pressure member.
Figure 33A:
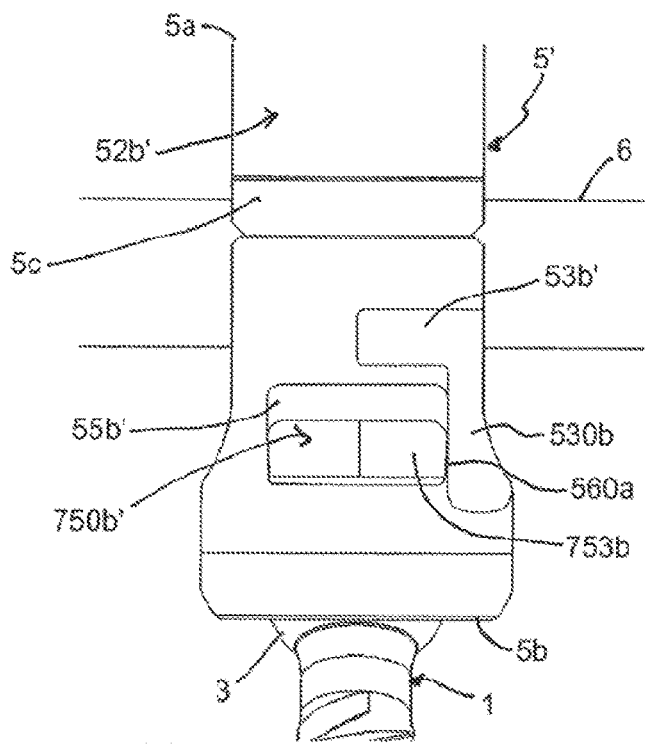
FIG. 33a shows a side view of the polyaxial bone anchoring device of FIGS. 18 to 31 in a locking position of the pressure member.

The lateral apertures 55a', 55b' are located symmetrically relative to the channel axis L in the middle of each leg 52a, 52b. They have a circumferential width that is greater than their axial height, so that their shape is elongate in the circumferential direction. As shown in FIGS. 32a and 33a, in a side-view, the width of the apertures 55a', 55b' in a circumferential direction increases slightly from the second end 5b towards the first end 5a of the receiving part 5'. The short side edges 560 of the apertures 55a', 55b' have inclined portions or ramps 560a that are inclined in such a manner that they narrow the apertures 55a', 55b' towards the second end 5b. More in detail, each aperture 55a', 55b' has two inclined portions 560a, one on each side edge 560. The inclined portions 560a form a first contact surface for cooperating with the pressure member 7'.

In addition, the receiving part 5' has engagement portions for the instrument in the form of circumferentially extending ribs 53a', 53b', that are arranged axially or rotationally symmetrical with respect to the central axis C, or asymmetrical in a plane extending through the central axis C and the channel axis L. That means, one rib 53a' is closer to one end of the substantially U-shaped recess 52 and the other rib 53b' is arranged closer to the second end of the substantially U-shaped recess 52. The ribs 53a', 53b' are located above an upper edge of the apertures 55a', 55b' towards the first end 5a and below the groove 5c. A circumferential extension of the ribs may be about half of the width of the apertures 55a', 55b'. Each rib 53a', 53b' continues at the side closer to the substantially U-shaped recess 52 into a longitudinal or axial rib or protrusion 530a, 530b that extends along a side of the aperture 55a', 55b', respectively. The longitudinal ribs 530a, 530b may have rounded end portions 531a, 531b that are adapted to the contour of the U-shaped recess 52 in the region of the base of the recess. As can be seen in particular in FIGS. 23 and 25, the longitudinal ribs 530a, 530b are configured to form abutments for the instrument when the instrument engages the circumferential ribs 53a', 53b'. Moreover, the longitudinal ribs 530a, 530b provide a stiffening structure for both legs 52a', 52b', to increase the strength of the receiving part 5'. This may be advantageous since the apertures 55a', 55b' are adapted to have a width sufficient to let the pressure member 7' pass therethrough.

As shown in detail in FIGS. 28 to 31, the pressure member 7' has a first end 7a forming an upper end and an opposite second end 7b forming a lower end. Adjacent to the upper end, a first portion 70' is provided that includes the cylindrical rod support surface 77 and extensions 750a', 750b' extending on both sides from the cylinder or rod channel axis L. The lateral extensions 750a', 750b' have a greatest width w in the direction of the channel axis L that permits insertion of the pressure member 7' through the apertures 55a', 55b'. The height in an axial direction of the lateral extensions 750a', 750b' is smaller than the height of the apertures 55a', 55b' such that the lateral extensions 750a', 750b' can move in an axial direction in the apertures 55a', 55b'.

Figure 30:
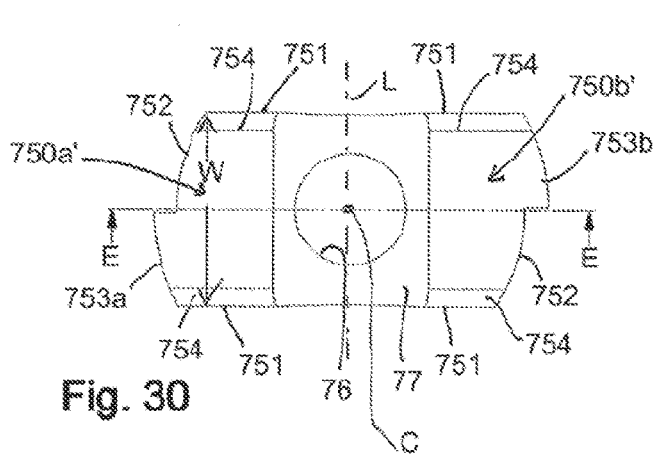
FIG. 30 shows a top view of the pressure member of FIGS. 28 and 29.
Figure 31:
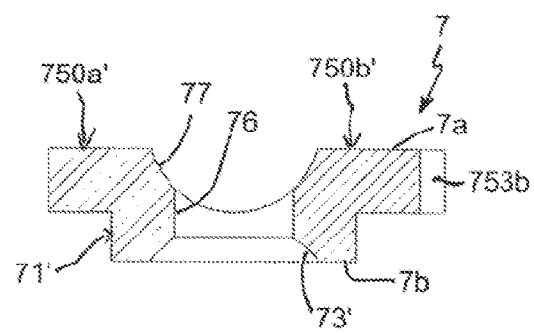
FIG. 31 shows a cross-sectional view of the pressure member of FIGS. 28 to 30, the cross-section taken along line E-E in FIG. 30.

In a top view, as depicted in FIG. 30, the lateral extensions 750a', 750b' have longitudinal sides 751 and transverse sides 752, the latter having preferably a circular segment-shaped or rounded contour that may be adapted to an outer contour of the receiving part 5'. On each transverse side 752, an engagement portion 753a, 753b, respectively, is provided that may also have a circular segment-shaped or rounded contour and that protrudes farther outward than the transverse side 752. The engagement portions 753a, 753b are arranged axially or rotationally symmetrical with respect to the central axis C of the pressure member 7'. The size of the pressure member 7' is such that when the pressure member 7' is mounted to the receiving part 5', the transverse sides 752 lie within the apertures 55a', 55b' and the engagement portions 753a, 753b protrude outwardly from the apertures 55a', 55b'. Moreover, in the mounted state, the engagement portion 753a is adjacent to the longitudinal rib 530a and the engagement portion 753b is adjacent to the longitudinal rib 530b.

The longitudinal sides 751 may be inclined so that, in a side-view as depicted in FIGS. 32a to 33b, the lateral extensions 750a', 750b' form wedges that interact with the inclined surfaces 560a of the apertures 55a', 55b'. Thus, at least a portion of the longitudinal sides 751 of the first portion 70' of the pressure member 7' form second contact surfaces that cooperate with the first contact surfaces in the form of the inclined portions 560a in the lateral apertures 55a', 55b'.

The edges 754 between the upper end 7a and the lateral sidewalls 751 may be bevelled or rounded to facilitate the lateral insertion of the pressure member 7' into the receiving part 5'.

Moreover, the pressure member 7' has, adjacent to the second end 7b, a second portion 71' that defines a spherical recess 73' to accommodate a portion of the head 3 therein. An outer surface of the second portion 71' is substantially cylindrical with an outer diameter slightly smaller than an inner diameter of the first coaxial bore 50a', so that the second portion 71' can slide in the bore 50a'. At both sides of the rod support surface 77, the second portion 71' has a flat sidewall 78 that is substantially flush with the longitudinal sides 751 of the lateral extensions 750a', 750b'. A total height of the pressure member 7' between the upper end 7a and the lower end 7b is slightly smaller than the axial height of the apertures 55a', 55b', such that the pressure member 7' can be laterally inserted through the apertures 55a', 55b'.

Figure 21:
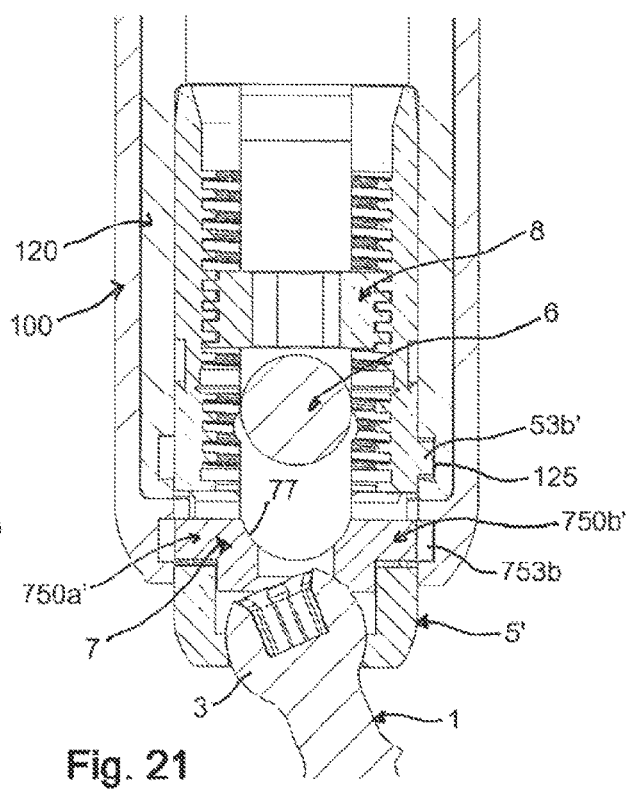
FIG. 21 shows a cross-sectional view of the polyaxial bone anchoring device of FIGS. 18 to 20 with the instrument of FIGS. 13 and 14 attached thereto.
Figure 22:
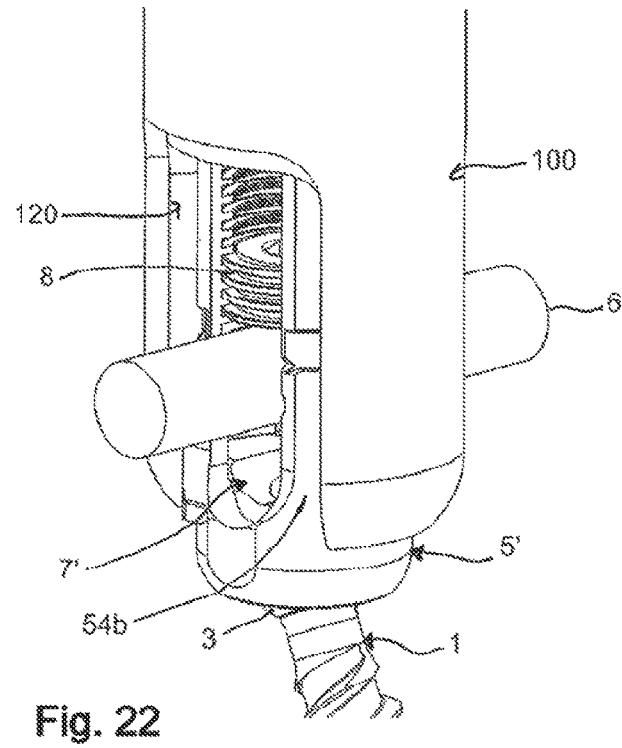
FIG. 22 shows a perspective view of the polyaxial bone anchoring device with the attached instrument as shown in FIG. 21.
Figure 23:
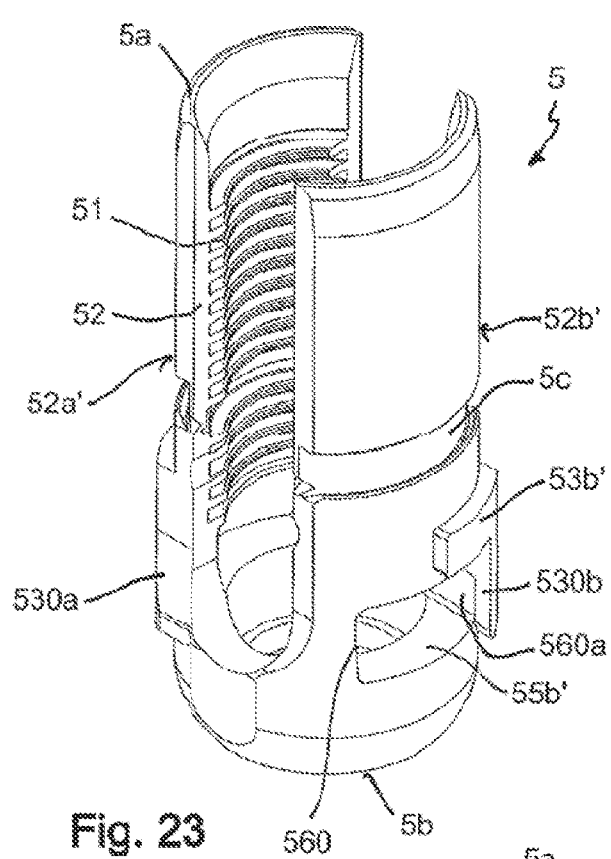
FIG. 23 shows a perspective view from a top of a receiving part of the polyaxial bone anchoring device of FIGS. 18 to 22.
Figure 24:
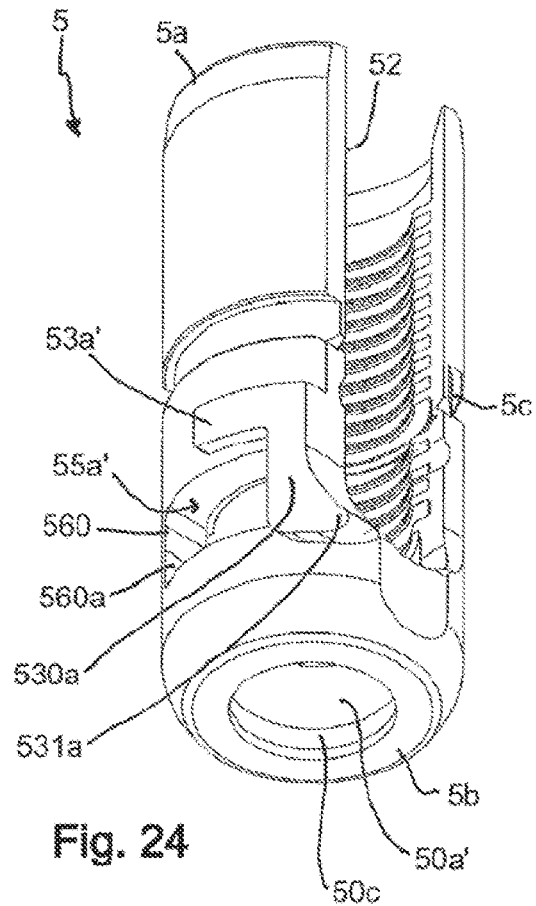
FIG. 24 shows a perspective view from a bottom of the receiving part of FIG. 23.
Figure 25:
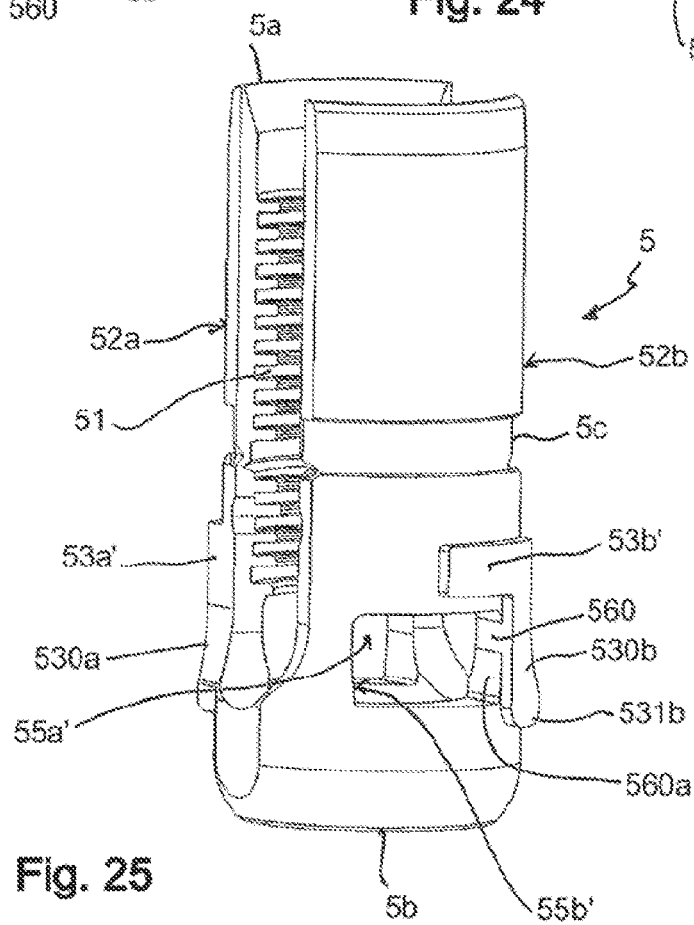
FIG. 25 shows a perspective view from a side the receiving part of FIGS. 23 and 24.
Figure 26:
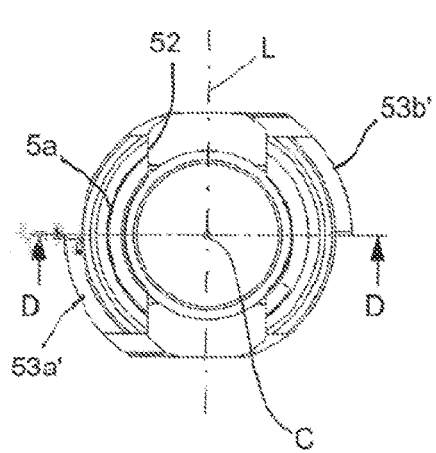
FIG. 26 shows a top view of the receiving part of FIGS. 23 to 25.
Figure 27:
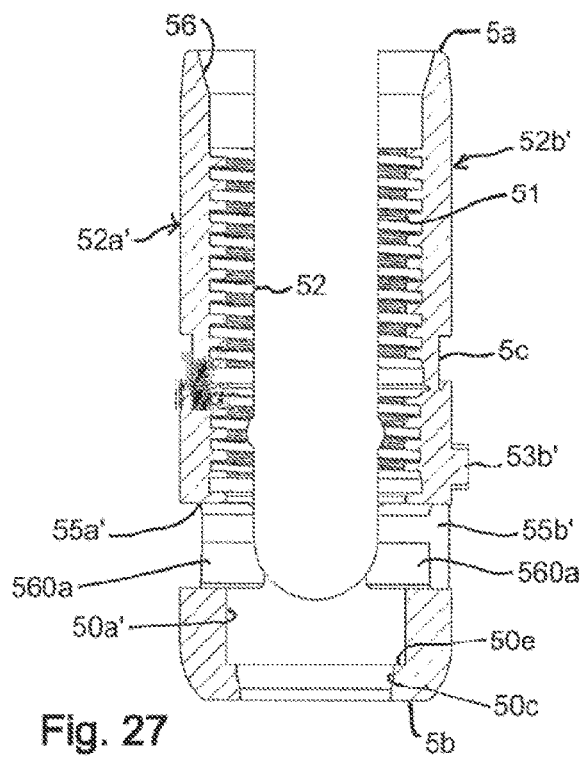
FIG. 27 shows a cross-sectional view of the receiving part of FIGS. 23 to 26, the cross-section taken along line D-D in FIG. 26.
Figure 28:
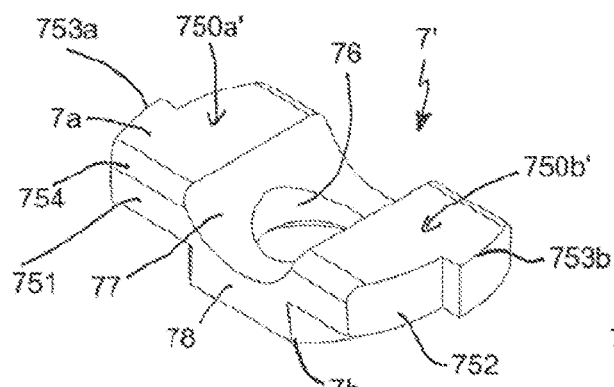
FIG. 28 shows a perspective view from a top of a pressure member of the polyaxial bone anchoring device of FIGS. 18 to 22.
Figure 29:
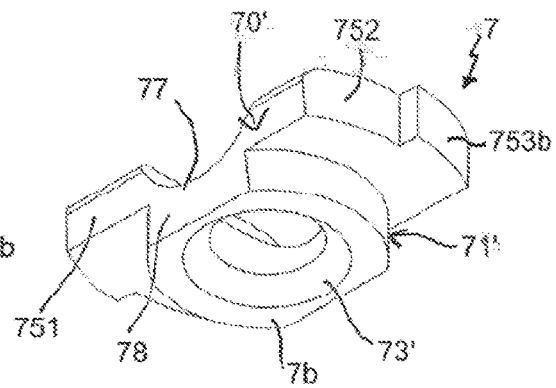
FIG. 29 shows a perspective view from a bottom of the pressure member of FIG. 28.
Figure 32B:
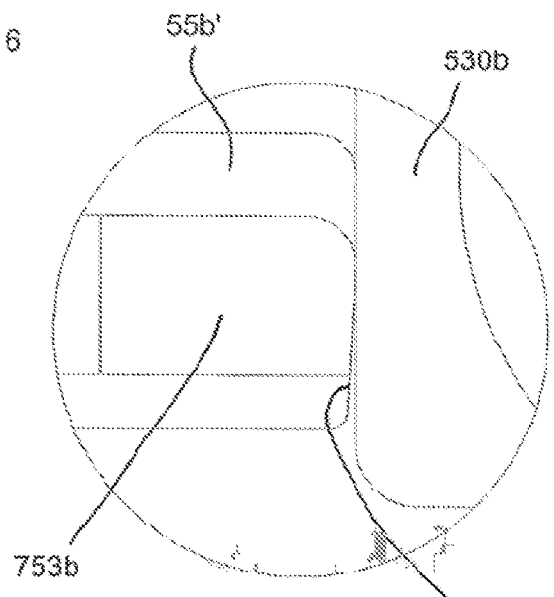

The bone anchoring device according to this embodiment is assembled by first inserting the bone anchoring element 1 through the top end 5a of the receiving part 5' until the head 3 rests in the seat 50c. Then the pressure member 7' is inserted laterally through the apertures 55a', 55b', such that the spherical recess 73' faces the head 3 and the rod support surface 77 is aligned with the U-shaped recess. When the pressure member 7' has been inserted, it is in an upper position where it does not exert enough pressure onto the head to lock the head, such that the head 3 is pivotable in the receiving part 5'. This is the non-locking position as depicted in FIGS. 32a and 32b. The longitudinal sides 751 do not yet have substantial contact with the inclined surfaces 560a within the apertures 55a', 55b'. To achieve the locking position of the pressure member 7', an instrument similar to the instrument described in FIGS. 13 and 14 may be used. It shall be noted that the instrument used for this embodiment may be adapted to the engagement portions 753a, 753b of the pressure member 7', for example, as shown in FIG. 21. The instrument is placed on the receiving part 5', so that it first covers the rib-free surfaces 54a, 54b, and is then rotated so that the inner tube 120 engages the ribs 53a', 53b' and the outer tube engages the engagement portions 753a, 753b.

Further rotation of the instrument is stopped by the abutment of the outer tube at the longitudinal ribs 530a, 530b.

Figure 33B:
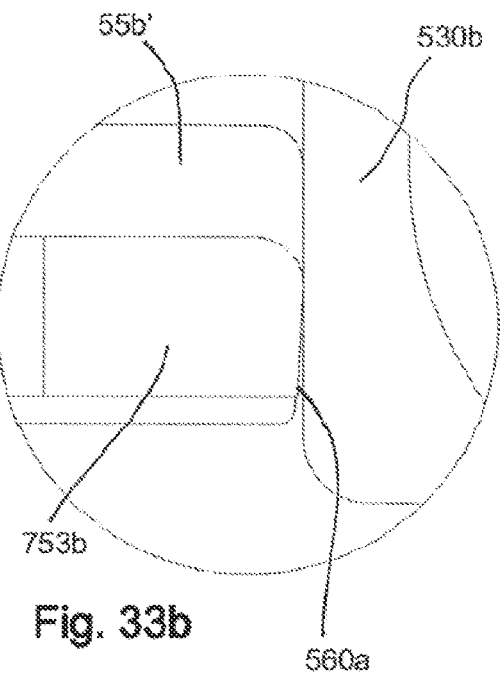

By moving the outer tube downward relative to the inner tube, the locking position as depicted in FIGS. 33a and 33b, can be achieved. In the locking position, the pressure member 7' exerts a pressure onto the head such that the head is clamped between the pressure member and the seat 50c. The locking position is maintained by the friction between the cooperating first and second surfaces of the receiving part 5' and the pressure member 7'. The pressure member 7' is maintained in the locking position even if the instrument is removed. By moving the outer tube back upwards relative to the inner tube, the pressure member 7' can be moved out of the locking position and the locking of the head 3 is released.

A still further embodiment of the polyaxial bone anchoring device will be described with reference to FIGS. 34 to 43. The polyaxial bone anchoring device here is configured as a bottom-loading bone anchoring device, wherein the bone anchoring element can be inserted into the receiving part from the bottom end 5b of the receiving part. The same or similar portions are indicated with the same reference numerals as in the previous embodiments, and the descriptions thereof will not be repeated. The receiving part 5" has a first coaxial bore 50a" that widens into an accommodation space 50b", in which the head 3 and a portion of the pressure member encompassing the head 3 can be accommodated. The accommodation space 50b" narrows towards the bottom end 5b in a narrowing portion 50c" that may be tapered or spherical or otherwise narrowing. In the accommodation space 50b", an edge 50d may be present that may serve for guiding a portion of the pressure member 7" to the narrowing portion 50c".

The receiving part 5" is mirror-symmetrical with respect to a plane extending through the central axis C and including the longitudinal axis L of the U-shaped recess 52. A pair of opposite apertures 55a", 55b" are provided in the legs 52a", 52b". The apertures 55a", 55b" have an elongate shape in the axial direction and serve for receiving pins. At an inner edge of each aperture 55a", 55b", protrusions 570 may be formed, preferably on both inner edges of each of the apertures 55a", 55b", that narrow the elongate apertures 55a", 55b" so that the pins can be temporarily held at a lowermost position once they have passed the protrusions 570.

At the outer surface of the receiving part 5", substantially in the middle of each of the legs 52a", 52b", and above the apertures 55a", 55b", engagement portions in the form of protrusions 53a", 53b" are provided that serve for engagement with an instrument. The engagement portions 53a", 53b" may have a triangular contour with the tip of the triangle facing towards the first end 5a, thereby exhibiting slanted edges for facilitating coupling with an instrument. A lower end 535 may be inclined so that an acute angle is formed between the engagement portions 53a", 53b" and the outer wall of the receiving part, also for facilitating engagement with the instrument. To the left and to the right of each engagement portion 53a", 53b" longitudinal grooves 536 are arranged for guiding the instrument. It shall be noted that the instrument used for this embodiment is adapted to the engagement portions, and is preferably configured to be placed over the receiving part and to engage the engagement portions 53a", 53b" only by downward movement.

The receiving part 5" lacks the extended legs. It shall be noted, however, that it is conceivable that the receiving part 5" also has the extended legs and the groove 5c for breaking-off the extended legs.

Figure 34:
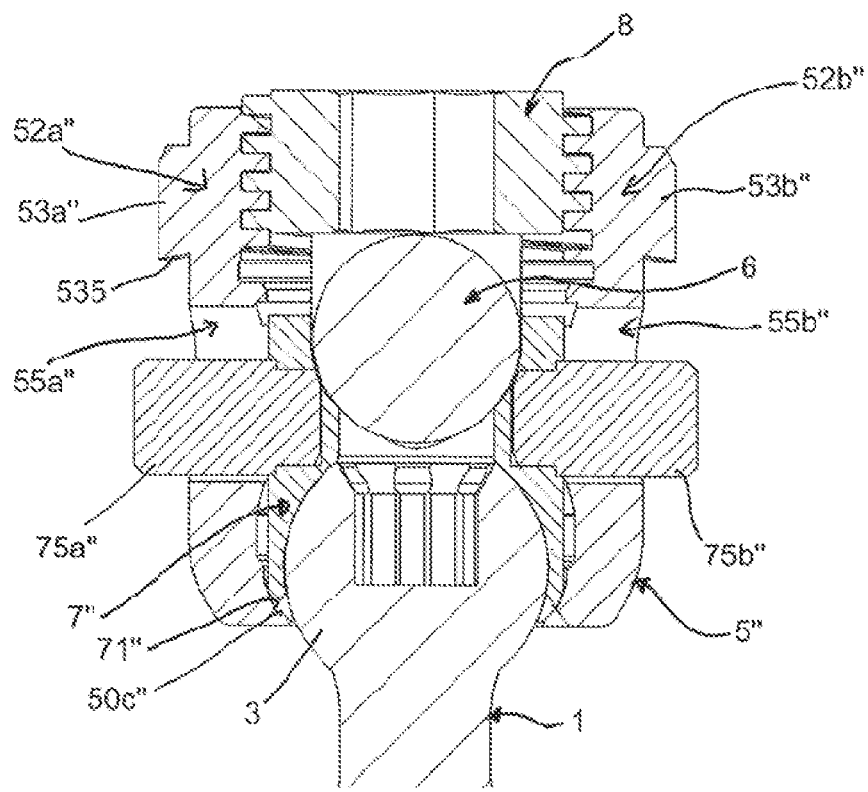
FIG. 34 shows a cross-sectional view of a polyaxial bone anchoring device according to a still further embodiment, wherein the cross-section is taken in a plane perpendicular to the rod axis and extending through a central axis and through a middle of legs of the receiving part.

The pressure member 7" will be described, referring additionally to FIGS. 40 to 43. The pressure member 7" is a substantially cylindrical part, with a first or upper end 7a and an opposite second or lower end 7b. A rod support surface 77" is provided adjacent to the first end 7a. In this embodiment, the rod support surface 77" has a substantially V-shaped cross-section to support rods of different diameter. An outer diameter of the pressure member 7" is such that the pressure member can be inserted into the receiving part 5" through the first end 5a and slide in the first coaxial bore 50a". Adjacent to the second end 7b, a hollow interior chamber 73" is provided that is configured to accommodate at least a portion of the head 3, in particular to extend over the region of the head 3 with the greatest diameter. To permit the pressure member 7" to snap onto the head 3, a plurality of slits 74" render the pressure member in a region of the interior chamber 73" flexible. The slits 74" are open towards the second end 7b and may have any shape, for example, with enlarged end portions, to achieve the desired flexibility. Adjacent to the second end 7b, an outer surface portion 71" narrows towards the second end 7b. The narrowing portion 71" may be tapered or may narrow otherwise. As shown in FIG. 34, the narrowing portion 71" cooperates with the narrowing portion 50c" of the receiving part. Hence, the narrowing portions 50c" and 71" form first and second contact surfaces that hold the pressure member 7" by friction in the lowermost position, i.e., the locking position.

Two holes or recesses 78a", 78b" are provided at a distance from the first end 7a and to the left and the right of the rod support surface 77". The holes 78a, 78b are configured to receive pins 75a", 75b", preferably in a press-fit manner, as shown in FIG. 34. The holes may be closed towards to the rod support surface 77".

The polyaxial bone anchoring device is assembled by inserting the pressure member 7" through the first end 5a of the receiving part 5", until its lower end extends into the accommodation space 50b". Then the pins 75a", 75b" are mounted through the apertures 55a", 55b" such that they are pressed into the holes 78a", 78b", whereby the pressure member 7" is held in the receiving part 5". The head 3 is inserted from the second end 5b of the receiving part 5" and enters the chamber 73" of the pressure member 7". The abutment of the pins 75a", 75b" at the upper edge of the apertures 55a", 55b" prevents the pressure member 7" from escaping through the first end 5a when the head 3 is inserted. In this condition, the head 3 is still pivotable, hence it is a non-locking position of the pressure member 7".

Figure 35:
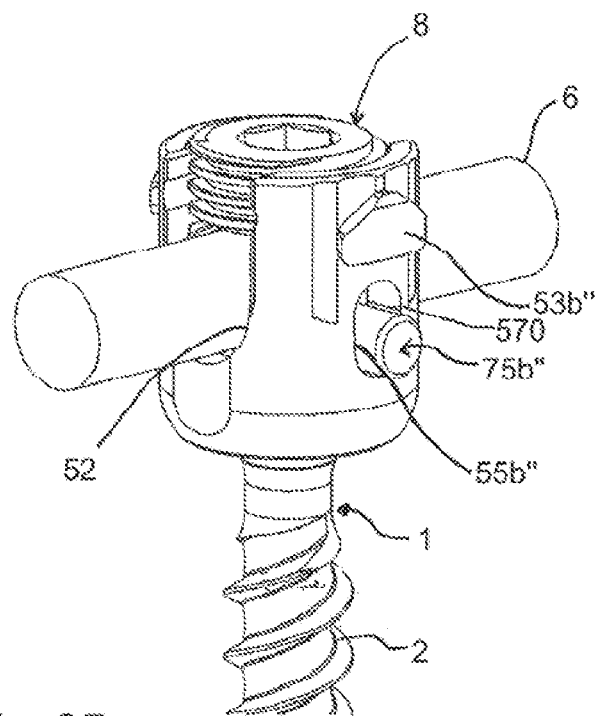
FIG. 35 shows a perspective view of the polyaxial bone anchoring device of FIG. 34 in an assembled state.
Figures 36, 37:
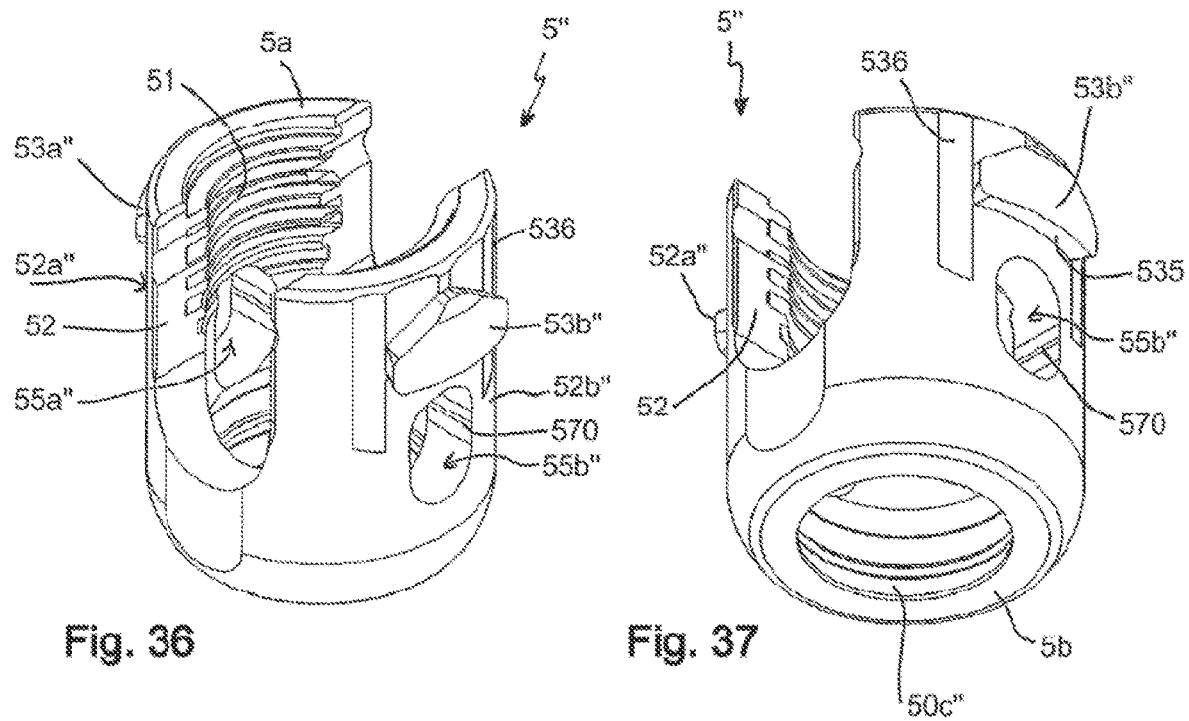
FIG. 36 shows a perspective view from a top of a receiving part of the polyaxial bone anchoring device of FIGS. 34 and 35.
FIG. 37 shows a perspective view from a bottom of the receiving part of FIG. 36.
Figures 38, 39:
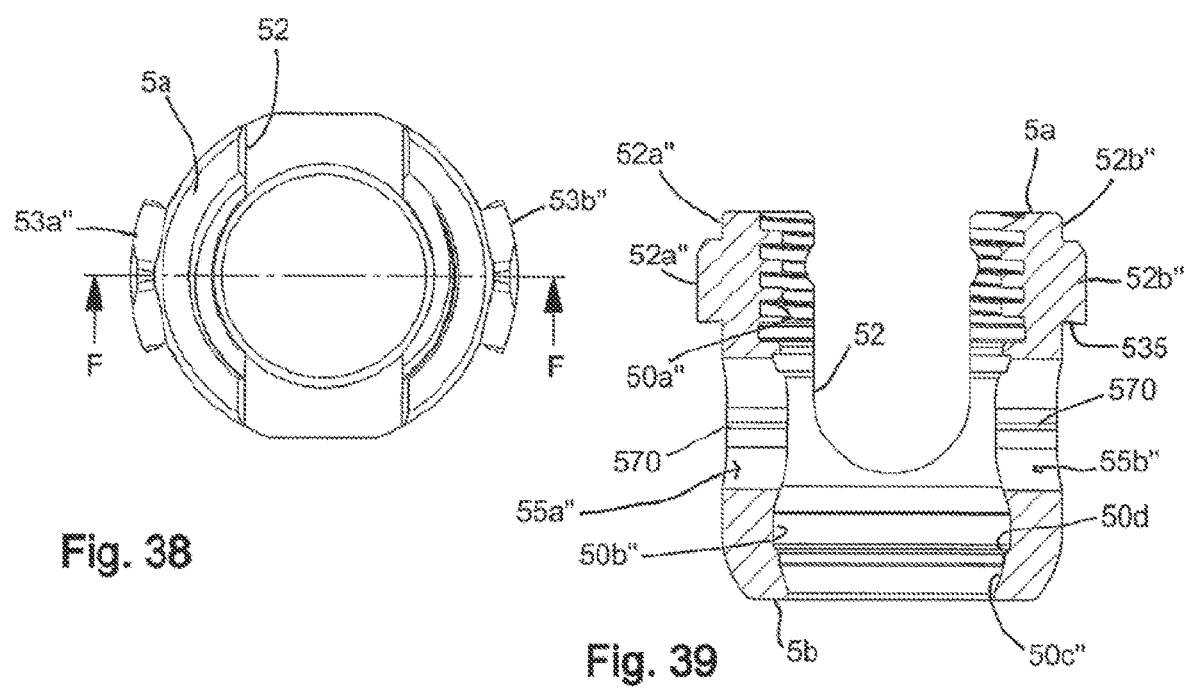
FIG. 38 shows a top view of the receiving part of FIGS. 36 and 37.
FIG. 39 shows a cross-sectional view of the receiving part of FIGS. 36 to 38, the cross-section taken along line F-F in FIG. 38.
Figure 40:
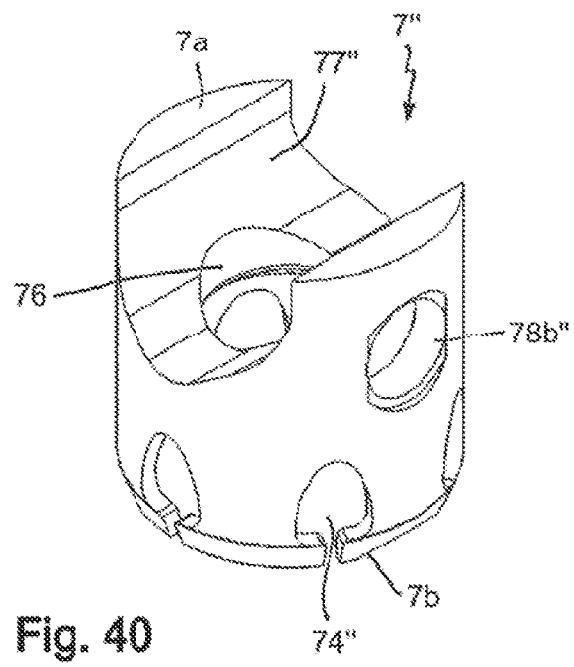
FIG. 40 shows a perspective view from a top of a pressure member of the polyaxial bone anchoring device of FIGS. 34 and 35.
Figure 41:
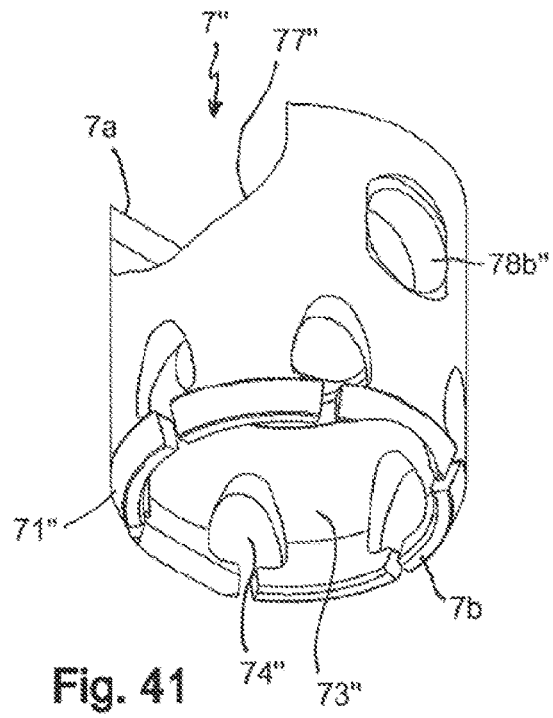
FIG. 41 shows a perspective view from a bottom of the pressure member of FIG. 40.
Figure 42:
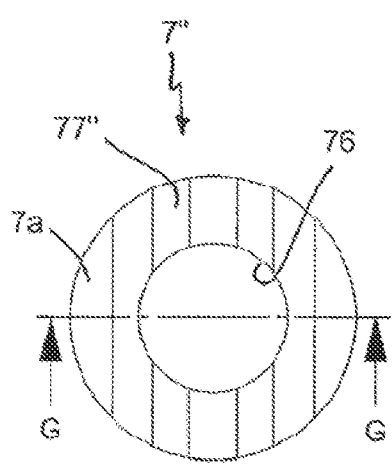
FIG. 42 shows a top view of the pressure member of FIGS. 40 and 41.
Figure 43:
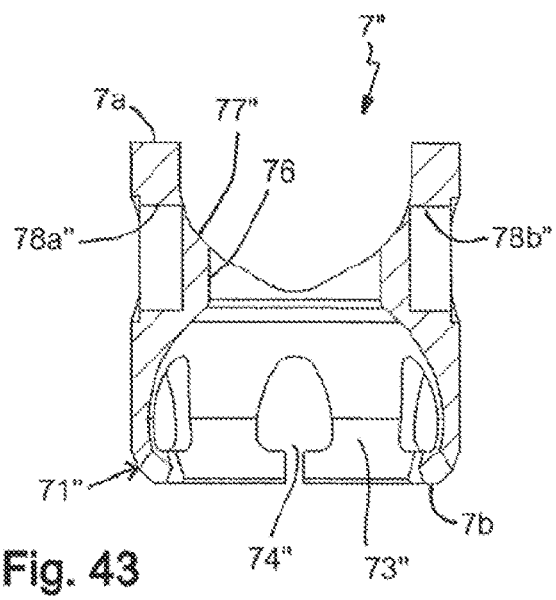
FIG. 43 shows a cross-sectional view of the pressure member of FIGS. 40 to 42, the cross-section taken along line G-G in FIG. 42.

Using an instrument (not shown) that engages the engagement portions 53a", 53b", the pressure member 7" can be moved downward until the narrowing portion 71" of the pressure member 7" and the narrowing portion 50c" of the receiving part 5" frictionally engage, thereby clamping or locking the head 3. In this locking position, the pins have passed the protrusions 570 and are located at the lowermost portion within the apertures 55a", 55b" as shown in FIGS. 34 and 35. The head 3 remains locked due to the friction between the narrowing portions and due to the pins being positioned below the protrusions 570, even if the instrument is removed. The pressure member 7" can be moved back to the non-locking position using the instrument.

Modifications of the above-described embodiments may also be contemplated. For example, other mechanisms of engagement between the pressure member and the receiving part that hold the pressure member in the locking position, may be used. The frictionally engaging surfaces may be provided elsewhere in the receiving part and the pressure member. The shape of the apertures and the pins is only exemplary, and other shapes may be conceivable.

Instead of ribs, other engagement portions for an instrument can be provided on the receiving part, for example grooves that cooperate with ribs on the instrument or combinations of ribs and grooves. The receiving part can also have apertures and engagement portions that are all mirror-symmetrical to a plane extending through the channel axis and the central axis, and the pressure member may be adapted thereto.

The bone anchoring device according to other embodiments of the invention can be provided in further modified forms. For example, the head of the bone anchoring element can have another shape, such as, for example, a cylindrical shape or a spherical shape with flattened sides, wherein a mono-planar device is provided that allows pivoting of the anchoring element in a single plane. The pressure member can also be shaped such that it can be inserted from the lower end of the receiving part.

In some embodiments, the receiving part can have an inclined lower end or can be otherwise asymmetric to allow for a greater angulation of an inserted head in one direction.

The extended tabs can be omitted in the embodiments, or all embodiments can have the extended tabs.

In addition, in some embodiments, other kinds of fixation members can also be used, for example, non-threaded fixation members that have an alternative advancement structure. In addition, all kinds of bone anchoring elements can be used, such as, for example, nails or bone anchors with barbs.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device for coupling a rod to a bone, the bone anchoring device comprising:
   a bone anchoring element comprising a shank for anchoring to the bone and a head;
   a receiving part configured to receive the head, the receiving part having a first end and a second end below the first end, a central axis extending through the first end and the second end, two legs at the first end for receiving the rod therebetween, and an opening that extends through a side of the receiving part to an outer surface of the receiving part; and
   a monolithic pressure member movable in the receiving part and configured to directly contact the head to exert pressure on the head, the pressure member comprising at least one engagement portion;
   wherein when the head and the pressure member are in the receiving part, the engagement portion of the pressure member is configured to extend laterally through the opening of the receiving part and radially outwardly past both a portion of the outer surface that defines a region of the opening located below the engagement portion and a portion of the outer surface that defines a region of the opening located circumferentially to one side of the engagement portion, and is directly engageable from outside the bone anchoring device by an instrument to move the engagement portion for adjusting the pressure member from a non-locking position in which the head is pivotable in the receiving part to a locking position in which an angular position of the receiving part relative to the bone anchoring element is locked.

2. The polyaxial bone anchoring device of claim 1, wherein the two legs define a recess at the first end for receiving the rod.

3. The polyaxial bone anchoring device of claim 2, wherein the opening of the receiving part is different and spaced apart from the recess for receiving the rod.

4. The polyaxial bone anchoring device of claim 1, wherein the opening extends laterally through one of the legs.

5. The polyaxial bone anchoring device of claim 1, wherein the outer surface of the receiving part further comprises a portion that defines a region of the opening located above the engagement portion of the pressure member.

6. The polyaxial bone anchoring device of claim 5, wherein the engagement portion of the pressure member further extends radially outwardly past the portion of the outer surface that defines the region of the opening located above the engagement portion of the pressure member.

7. The polyaxial bone anchoring device of claim 1, wherein the opening forms upper and lower stops for limiting axial movement of the engagement portion of the pressure member relative to the receiving part.

8. The polyaxial bone anchoring device of claim 1, wherein at least part of the pressure member is insertable from outside the receiving part through the opening into the receiving part.

9. The polyaxial bone anchoring device of claim 1, wherein when a longitudinal axis of the bone anchoring element is aligned with the central axis of the receiving part, the pressure member is configured to at least partially encompass a portion of the head having the greatest width of the head measured in a direction perpendicular to the longitudinal axis of the bone anchoring element.

10. The polyaxial bone anchoring device of claim 1, wherein the receiving part comprises at least one further engagement portion that is engageable by the instrument.

11. The polyaxial bone anchoring device of claim 1, further comprising a fixation member for fixing the rod and the head simultaneously relative to the receiving part.

12. The polyaxial bone anchoring device of claim 11, wherein when the pressure member is at the locking position and the fixation member is not engaged with the receiving part, the pressure member is configured to remain at the locking position.

13. A system comprising the polyaxial bone anchoring device of claim 1 and an instrument comprising a first engagement surface for engaging the receiving part and a second engagement surface for engaging the engagement portion of the pressure member to move the engagement portion for adjusting the pressure member from the non-locking position to the locking portion.

14. The system of claim 13, wherein the second engagement surface of the instrument is further configured to move the engagement portion for adjusting the pressure member from the locking position back to the non-locking position.

15. The system of claim 13, wherein the instrument comprises a first tubular member comprising the first engagement surface and a second tubular member displaceable relative to the first tubular member and comprising the second engagement surface.

16. The system of claim 13, wherein the instrument is configured to engage at least one of the receiving part or the pressure member by rotating the instrument relative to the bone anchoring device.

17. A method of coupling a rod to a bone using a polyaxial bone anchoring device comprising a bone anchoring element comprising a shank and a head, a receiving part configured to receive the head, the receiving part having a first end and a second end below the first end, a central axis extending through the first end and the second end, two legs at the first end for receiving the rod therebetween, and an opening that extends through a side of the receiving part to an outer surface of the receiving part, a monolithic pressure member movable in the receiving part and configured to directly contact the head to exert pressure on the head, the pressure member comprising at least one engagement portion, and a fixation member, the method comprising:
- anchoring the shank of the bone anchoring element to the bone or vertebra;
- pivoting the receiving part relative to the bone anchoring element when the head and the pressure member are in the receiving part, where the engagement portion of the pressure member is configured to extend laterally through the opening of the receiving part and radially outwardly past both a portion of the outer surface that defines a region of the opening located below the engagement portion and a portion of the outer surface that defines a region of the opening located circumferentially to one side of the engagement portion, and is directly engageable from outside the bone anchoring device by an instrument;
- moving the engagement portion with the instrument to adjust the pressure member from a non-locking position in which the head is pivotable in the receiving part to a locking position in which an angular position of the receiving part relative to the bone anchoring element is locked;
- adjusting the rod between the legs of the receiving part; and
- advancing the fixation member in the receiving part to fix the rod in the recess.

18. The method of claim 17, wherein the two legs define a recess at the first end for receiving the rod, and wherein the opening of the receiving part is spaced apart from the recess and extends laterally through one of the legs.

19. The method of claim 17, wherein the instrument is further configured to adjust the pressure member from the locking position back to the non-locking position.

20. A system comprising:
- a polyaxial bone anchoring device for coupling a rod to a bone, the bone anchoring device comprising:
  - a bone anchoring element comprising a shank for anchoring to the bone and a head;
  - a receiving part configured to receive the head, the receiving part having a first end and a second end below the first end, a central axis extending through the first end and the second end, and two legs defining a recess at the first end for receiving the rod, wherein at least one of the legs further defines an opening that extends through the leg to an outside of the receiving part; and
  - a pressure member movable in the receiving part to exert pressure on the head, the pressure member comprising at least one engagement portion; and
- an instrument comprising a first engagement surface for engaging the receiving part and a second engagement surface for engaging the engagement portion of the pressure member;
- wherein when the head and the pressure member are in the receiving part, the engagement portion is configured to extend at least partially into the opening of the leg and is directly engageable from outside the receiving part by the second engagement surface of the instrument, such that the second engagement surface of the instrument is configured to move the engagement portion along a direction parallel to the central axis relative to the receiving part for adjusting the pressure member both from a non-locking position in which the head is pivotable in the receiving part to a locking position in which an angular position of the receiving part relative to the bone anchoring element is locked, and from the locking position back to the non-locking position.

21. The system of claim 20, wherein the pressure member is configured to be held at the locking position by the instrument while the recess for the rod remains sufficiently unobstructed for the rod to extend and move therethrough.

22. The system of claim 20, wherein the instrument is configured to engage at least one of the receiving part or the pressure member by rotating the instrument relative to the bone anchoring device.

* * * * *